US009550789B2

(12) United States Patent
Moriarty et al.

(10) Patent No.: US 9,550,789 B2
(45) Date of Patent: Jan. 24, 2017

(54) HALOGENATED INDOLE AND BENZOFURAN DERIVATIVES OF ISOQUINUCLIDENE AND PROCESSES FOR PREPARING THEM

(71) Applicant: DemeRx, Inc., Fort Lauderdale, FL (US)

(72) Inventors: Robert M. Moriarty, Michiana Shores, IN (US); Mark Kinch, San Diego, CA (US)

(73) Assignee: DEMERX, INC., Fort Lauderdale, FL (US)

( * ) Notice: Subject to any disclaimer, the term of this patent is extended or adjusted under 35 U.S.C. 154(b) by 0 days.

(21) Appl. No.: 14/741,134

(22) Filed: Jun. 16, 2015

(65) Prior Publication Data

US 2015/0368255 A1    Dec. 24, 2015

Related U.S. Application Data

(60) Provisional application No. 62/013,771, filed on Jun. 18, 2014.

(51) Int. Cl.
    C07D 487/22    (2006.01)

(52) U.S. Cl.
    CPC .................... C07D 487/22 (2013.01)

(58) Field of Classification Search
    CPC .................................................. C07D 487/22
    See application file for complete search history.

(56) References Cited

U.S. PATENT DOCUMENTS

| | | | |
|---|---|---|---|
| 2,813,873 A | 11/1957 | Janot et al. |
| 3,516,989 A | 6/1970 | Sallay |
| 3,557,126 A | 1/1971 | Sallay |
| 3,574,220 A | 4/1971 | Sallay |
| 3,639,408 A | 2/1972 | Nagata et al. |
| 3,715,361 A | 2/1973 | Epstein et al. |
| 3,875,011 A | 4/1975 | Rubenstein et al. |
| 4,107,288 A | 8/1978 | Oppenheim et al. |
| 4,272,541 A | 6/1981 | Kotick et al. |
| 4,375,414 A | 3/1983 | Strahilevitz |
| 4,444,758 A | 4/1984 | Scherschlicht et al. |
| 4,462,941 A | 7/1984 | Lee et al. |
| 4,464,378 A | 8/1984 | Hussain |
| 4,499,096 A | 2/1985 | Lotsof |
| 4,573,995 A | 3/1986 | Chen et al. |
| 4,587,243 A | 5/1986 | Lotsof |
| 4,604,365 A | 8/1986 | O'Neill et al. |
| 4,620,977 A | 11/1986 | Strahilevitz |
| 4,626,539 A | 12/1986 | Aungst et al. |
| 4,661,492 A | 4/1987 | Lewis et al. |
| 4,668,232 A | 5/1987 | Cordes et al. |
| 4,806,341 A | 2/1989 | Chien et al. |
| 4,857,523 A | 8/1989 | Lotsof |
| 5,026,697 A | 6/1991 | Lotsof |
| 5,075,341 A | 12/1991 | Mendelson et al. |
| 5,145,684 A | 9/1992 | Liversidge et al. |
| 5,149,538 A | 9/1992 | Granger et al. |
| 5,152,994 A | 10/1992 | Lotsof |
| 5,283,247 A | 2/1994 | Dwivedi et al. |
| 5,290,784 A | 3/1994 | Qu et al. |
| 5,316,759 A | 5/1994 | Rose et al. |
| 5,382,657 A | 1/1995 | Karasiewicz et al. |
| 5,426,112 A | 6/1995 | Zagon et al. |
| 5,552,406 A | 9/1996 | Mendelson et al. |
| 5,574,052 A | 11/1996 | Rose et al. |
| 5,578,645 A | 11/1996 | Askanazi et al. |
| 5,580,876 A | 12/1996 | Crain et al. |
| 5,591,738 A | 1/1997 | Lotsof |
| 5,618,555 A | 4/1997 | Tokuda et al. |
| 5,703,101 A | 12/1997 | Rose et al. |
| 5,726,190 A | 3/1998 | Rose et al. |
| 5,760,044 A | 6/1998 | Archer |
| 5,861,422 A | 1/1999 | Rose et al. |
| 5,865,444 A | 2/1999 | Kempf et al. |
| 5,925,634 A | 7/1999 | Olney |
| 5,935,975 A | 8/1999 | Rose et al. |
| 6,211,360 B1 | 4/2001 | Glick et al. |
| 6,291,675 B1 | 9/2001 | Coop et al. |
| 6,348,456 B1 | 2/2002 | Mash et al. |
| 6,451,806 B2 | 9/2002 | Farrar |
| 6,806,291 B1 | 10/2004 | Sunkel et al. |
| 6,864,271 B2 | 3/2005 | Bazan et al. |
| 7,220,737 B1 | 5/2007 | Mash |
| 7,754,710 B2 | 7/2010 | Mash |
| 8,017,151 B2 | 9/2011 | Batrakova et al. |

(Continued)

FOREIGN PATENT DOCUMENTS

CA    2039197    9/1995
DE    22 17 132    10/1972

(Continued)

OTHER PUBLICATIONS

Total synthesis of ibogaine, epiibogaine and their analogues. Jana et al. Tetrahedron, 2012, 68, 7155-7165.*
Office Action on Chinese Application 201380004353.2, mailed Feb. 22, 2016 English Translation Provided.
Jana et al., "Reductive Heck coupling: an efficient approach toward the iboga alkaloids. Synthesis of ibogamine, epiibogamine and iboga analogs," Tetrahedron Letters 53 (2012, pp. 1671-1674.
Nakano et al., "A novel chiral oxazolidine organocatalyst for the synthesis of an oseltamivir intermediate using a highly enantioselective Diels-Alder reaction of 1,2-dihydropyridine," Chemical Communications, vol. 46, No. 26, Jan. 1, 2010, pp. 4827-4829.
Search Report issued on EP Application 13741387.8, mailed Oct. 21, 2015.
Ala-Hurula, et al. "Erogotamine Abuse: Results of Ergotamine Discontinuation, with Special Reference to the Plasma Concentrations," Cephalalgia, 2:4 1982, abstract only.
Ala-Hurula, et al. "Tolfenamic Acid and Ergotamine Abuse," Headache, 21:6, 1981, abstract only.

(Continued)

Primary Examiner — Brian McDowell
(74) Attorney, Agent, or Firm — Foley & Lardner LLP

(57) ABSTRACT

Provided herein are halogenated indole and benzofuran derivatives of isoquinuclidene and intermediates thereto, and processes, preferably enantioselective processes, for preparing such derivatives including processes for preparing (−) and (+) noribogaine, in substantially enantiomerically pure forms.

13 Claims, No Drawings

(56) References Cited

U.S. PATENT DOCUMENTS

| | | | |
|---|---|---|---|
| 8,178,524 | B2 | 5/2012 | Mash |
| 8,362,007 | B1 | 1/2013 | Mash et al. |
| 8,741,891 | B1 | 6/2014 | Mash |
| 8,765,737 | B1 | 7/2014 | Mash et al. |
| 8,802,832 | B2 | 8/2014 | Mash et al. |
| 2006/0051317 | A1 | 3/2006 | Batrakova et al. |
| 2010/0311722 | A1 | 12/2010 | Mash |
| 2010/0311723 | A1 | 12/2010 | Mash |
| 2010/0311725 | A1 | 12/2010 | Mash |
| 2012/0083485 | A1 | 4/2012 | Mash |
| 2013/0131046 | A1 | 5/2013 | Moriarty et al. |

FOREIGN PATENT DOCUMENTS

| | | |
|---|---|---|
| GB | 0 841 697 | 7/1960 |
| GB | 0 924 042 | 4/1962 |
| GB | 1 256 914 | 12/1971 |
| GB | 1 378 348 | 12/1974 |
| GB | 2 271 059 | 4/1994 |
| JP | 04-221315 | 8/1992 |
| JP | 2010-229097 A | 10/2010 |
| JP | 2011-068587 A | 4/2011 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/03127 A1 | 2/1996 |
| WO | WO-97/20847 | 6/1997 |
| WO | WO-2011/103007 | 8/2011 |
| WO | WO-2012/012764 A1 | 1/2012 |
| WO | WO-2013/028999 | 2/2013 |
| WO | WO-2013/085850 | 6/2013 |
| WO | WO-2013/112622 | 8/2013 |
| WO | WO-2013/112673 | 8/2013 |

OTHER PUBLICATIONS

Alexander. "A Procedure for Drug Screening Without the Need to Transport Urines Use of Ion Exchange Papers and Hem Agglutination Inhibition," Clinical Toxicology, 9:3, 1976, abstract only.

Alim, et al. "Open-Label, Dose Run-Up Study of Diethylpropion in Initial Cocaine Abstinence," Clinical Neuropharmacology, 17:2, 1994, abstract only.

Almeida. "Use and Abuse of Alcohol and Drugs a Clinical Study of Certain Aspects of Their Interrelationship," Boletin de la Oficina Sanitaria Panamericana, 88:1, 1980, abstract only.

Al-Shabanah, et al. "Gastric Antiulcer and Cytoprotective Effects of Cathinone, a Psychoactive Alkaloid of Khat (Catha Edulis Forsk.) And Amphetamine in Rats", Regulatory Peptides, 1994, abstract only.

Azevedo, et al. "Adrenergic Nerve Degeneration Induced by Condensation Products of Adrenaline and Acetaldehyde," Naunyn-Schmiedeberg's Archives of Pharmacology, 300:2, 1977, abstract only.

Bagal, et al. "Modulation of Morphine-Induced Antinociception by Ibogaine and Noribogaine," Brain Research, 741:1-2, 1996, pp. 258-262.

Bartlett, et al. "The Alkaloids of Tabernanthe iboga. Part IV. The Structures of Ibogamine, Ibogaine, Tabernanthine and Voacangine." Journal of the American Chemical Society, 80, 1958, pp. 126-136.

Batrakova. "Pluronic P85 Enhances the Delivery of Digoxin to the Brain: In Vitro And In Vivo Studies", The Journal of Pharmacology and Experimental Therapy, 296, 2001, pp. 551-557.

Baxter et al., Model Studies Probing the Amino-Claisen Rearrangement Approach to Hydroisoquinoline Synthesis, Development of Methods for Stereocontrolled Introduction of Reserpine E Ring Type Functionality, J Org Chem 1989, 54, 2893-2904.

Beaubrun. "The Diagnosis and Management of Acute Psychotic Reaction Due to Alcohol and Drugs", Caribbean Medical Journal, 36:1, 1975, abstract only.

Beck, et al. "Energy-Dependent Reduced Drug Binding as a Mechanism of Vinca Alkaloid Resistance in Human Leukemic Lymphoblasts", Molecular Pharmacology, 24:3, 1983, abstract only.

Benet, et al. "Pharmacokinetics: Biotransformation of Drugs." In Gilman et al. Goodman and Gilman's the Pharmacological Basis of Therapeutics, 1990, pp. 13-16.

Benoist, et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunology Immunotherapy , 30:5, 1989, abstract only.

Bert, et al. "Non-Amphetaminic Central Stimulation by Alkaloids from the Ibogaine and Vobasine Series", Planta Medicina, 54:3, 1988, abstract only.

Bhargava, et al. "Effects of ibogaine and noribogaine on the antinociceptive action of mu-, delta- and kappa-opioid receptor agonists in mice", Brain Research 752, 1997, pp. 234-238.

Blum, et al. "Peyote a Potential Ethnopharmacologic Agent for Alcoholism and Other Drug Dependencies Possible Biochemical Rationale", Clinical Toxicology, 11:4, 1977, abstract only.

Blum, et al. "Possible Role of Tetrahydroisoquinoline Alkaloids in Postalcohol Intoxication States", Annals of the New York Academy of Science, 273, 1976, abstract only.

Blum, et al. "Putative Role of Isoquinoline Alkaloids in Alcoholism: A Link to Opiates", Alcoholism: Clinical and Experimental Research, 2:2, 1978, abstract only.

Brady, et al. "Analgesic Effects of Intraventricular Morphine and Enkephalins in Nondependent and Morphine-Dependent Rats," Journal of Pharmacology and Experimental Therapy, 222:1, 1982, abstract only.

Buchi, et al. "The total synthesis of iboga alkaloids," Jounal of the American Chemical Society, 88, 1966, pp. 3099-3109.

Bundgaard. "Design of Prodrugs: Bioreversible Derivatives for Various Functional Groups and Chemical Entities." Design of Prodrugs, 1-10, 1985.

Bussel, et al. "Isolated Thrombocytopenia in Patients Infected with HIV Treatment with Intravenous Gamma Globulin," American Journal of Hematology, 28:2, 1988, abstract only.

Caldwell, et al. "The Biochemical Pharmacology of Abused Drugs. III. Cannabis, Opiates, and Synthetic Narcotics," Clinical Pharmacological Therapy, 16:6, 1974, abstract only.

Cankat. "Pharmacological Aspects of Drug Induced Headache", Functional Neurology, 7:6, 1992, abstract only.

Cappendijk, et al. "The Inhibitory Effect of Norharman on Morphine Withdrawal Syndrome in Rats: Comparison with Ibogaine." Behavioural Brain Research, 65, 1994, pp. 117-119.

Cappendijk, et al. "Inhibitory Effects of Ibogaine on Cocaine Self-Administration in Rats", European Journal of Pharmacology, 241:2-3, 1993, abstract only.

Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.

Cherny, et al., Opioid responsiveness of cancer pain syndromes caused by neuropathic or nociceptive mechanisms: a combined analysis of controlled, single-dose studies, Neurobiology 44, 1994, pp. 857-861.

Cheze, et al. "Determination of ibogaine and noribogaine in biological fluids and hair by LC-MS/MS after Tabernanthe iboga abuse", Forensic Science International, Elsevierscientific Publishers Ireland Ltd, IE, vol. 176, No. 1, Nov. 19, 2007, pp. 58-66.

Communication pursuant to Rule 161(2) and 162 EPC in EP Patent Application No. 13741381.1, dated Oct. 6, 2014.

(56) References Cited

OTHER PUBLICATIONS

Criel, et al. "Drug Dependent Red Cell Antibodies and Intravascular Haemolysis Occurring in Patients Treated with 9 Hydroxy-Methyl-Ellipticinium," British Journal of Haematology, 46:4, 1980, abstract only.

Damstrup, et al. "Retroperitoneal Fibrosis After Long-Term Daily Use of Ergotamine," International Urology and Nephrology, 18:3, 1986, abstract only.

Deecher, et al. "Mechanisms of Action of Ibogaine and Harmaline Congeners Based on Radioligand Binding Studies." Brain Research 571, 1992, pp. 242-247.

Diener, et al. "Analgesic-Induced Chronic Headache Long-Term Results of Withdrawal Therapy," Journal of Neurology, 236:1, 1989, abstract only.

Dierckx, et al. "Intraarterial Sodium Nitroprusside Infusion in the Treatment of Severe Ergotism," Clinical Neuropharmacology, 9:6, 1986, abstract only.

Dzoljic, et al. "Effect of Ibogaine on Naloxone-Precipitated Withdrawal Syndrome in Chronic Morphine-Dependent Rats," Archives Internationales de Pharmacodynamie et de Thérapie, 294, 1988, pp. 64-70.

Eberwine, et al. "Molecular Analysis of Cellular Responses to Opiate Use", Fidia Research Foundation Symposium Series 7 (Neurotransmitter Regulation of Gene Transcription) 1991, abstract only.

Elkind. "Drug Abuse and Headache", Medical Clinics of North America, 75:3, 1991, abstract only.

Evenson. "Developments in Therapeutic Drug Monitoring and Alkaloid Analysis", Federation Proceedings, 34:12, 1975, abstract only.

Faglia, et al. "Dihydroergocryptine in Management of Microprolactinomas," Journal of Clinical Endocrinology & Metabolism, 65:4, 1987, abstract only.

Fairchild, et al. "Keynote Address: Multidrug Resistance: A Pleiotropic Response to Cytotoxic Drugs," International Journal of Radiation, Oncology, Biology, & Physics, 20:2, 1991, abstract only.

Finkle. "Phencyclidine Identification by Thin-Layer Chromatography. A Rapid Screening Procedure for Emergency Toxicology", American Journal of Clinical Pathology, 70:2, 1978, abstract only.

First Office Action on Chinese Application 201380004353.2, issued Aug. 5, 2015.

Fonne-Pfister, et al. "Xenobiotic and Endobiotic Inhibitors of Cytochrome P-450dbl Function, the Target of the Debrisoquine / Sparteine Type Polymorphism," Biochemical Pharmacology, 37:20, 1988, abstract only.

Frances, et al. "Effects of Ibogaine on Naloxone-Precipitated Withdrawal in Morphine-Dependent Mice", Fundamental Clininical Pharmacology, 6:8-9, 1992, abstract only.

Gabr, et al. "Changes in Absolute Amount of Alkaloids in Datura-Metel Treated with Certain Growth Regulators", Herba Pot, 21:2, 1975, abstract only.

Garcia, et al. Chronic pain states: pathophysiology and medical therapy, Seminars in Arthritis and Rheumatism, 27, 1997, pp. 1-16.

Gennaro. "Remington: The Science and Practice of Pharmacy", Mack Publishing Col., vol. II, 1995, pp. 1736 & 1814.

George, et al. "Palliative medicine", Postgraduate Medical Journal, vol. 69, 1993, pp. 426-449.

Gifford, et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41:4, 1992, abstract only.

Glick, et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657, 1994, pp. 14-22.

Glick, et al. "Effect of Ibogaine on Acute Signs of Morphine Withdrawal in Rats: Independence from Tremor", Neuropharmacology, 31:5, 1992, abstract only.

Glick, et al. "Effects of Aftereffects of Ibogaine on Morphine Self-Administration in Rats", European Journal of Pharmacology, 195:3, 1991, abstract only.

Glick, et al. "Ibogaine-like effects of noribogaine in rats", Brain Research, 713, 1996, pp. 294-297.

Glick, et al. "Local Effects of Ibogaine on Extracellular Levels of Dopamine and Its Metabolites in Nucleus Accumbens and Striatum: Interactions with D-Amphetamine", Brain Research, 628:1-2, 1993, abstract only.

Gold, et al. "Effect of Methadone Dosage on Clonidine Detoxification Efficacy", American Journal Psychiatry, 137:3, 1980, abstract only.

Gothoni. "Harmine-, Lon-954- and 5-Hydroxytryptophan-Induced Tremors in Rats Withdrawn from Ethanol", Acta Pharmacologica et Toxicologica, Copenhagen, DK, 57:1, 1985, abstract only.

Gross. "Effect of Ergot Alkaloids on Serum Prolactin in Non-Psychotic Organic Brain Syndrome of the Elderly", Experimental Aging Research, 5:4, 1979, abstract only.

Gunn. "Relations Between Chemical Constitution, Pharmacological Actions, and Therapeutic Uses, in the Harmine Group of Alkaloids." From The Pharmacological Laboratory, University of Oxford, 1935, pp. 379-396.

Haber, et al. "Tetrahydroisoquinolines—Endogenous Products After Chronic Alcohol Abuse", Pharmazie, 47:1, 1992, abstract only.

Halikas, et al. "Treatment of Crack Cocaine Use with Carbamazepine", American Journal of Drug and Alcohol Abuse, 18:1, 1992, abstract only.

Hanks. "Opioid-responsive and opioid-non-responsive pain in cancer," British Medical Bulletin 47, 1991, pp. 718-731.

Hardman, et al. "Principles of Therapeutics," In Goodman, et al (ed.), "Goodman & Gilman's the Pharmacological Basis of Therapeutics." 9th Ed., McGraw-Hill, 1996, pp. 51, 57-58.

Harsing, et al. "Evidence that Ibogaine Releases Dopamine from the Cytoplasmic Pool in Isloated Mouse Striatum", Journal of Neural Transmission General Section, 96:3, 1994, abstract only.

Hearn, et al. "Identification and Quantitation of Ibogaine and an o-Demethylated Metabolite in Brain and Biological Fluids Using Gas Chromatography-Mass Spectrometry." Journal Analytical Toxicology, 19, 1995, pp. 427-434.

Heel, et al. "Buprenorphine: A Review of Its Pharmacological Properties and Therapeutic Efficacy", Drugs, 17:2, 1979, abstract only.

Hennessy et al., "Discovery of amniopiperidine-based Smac mimetics as IAP antagonists," Bioorg. Med. Chem. Lett., (2012), 22:1690-1694.

Henry, et al. "Reversible Cerebral Arteriopathy Associated with the Administration of Ergot Derivatives", Cephalalgia, 4:3, 1984, abstract only.

Ho, et al. "Metabolism of Harmaline in Rats." Biochemical Pharmacology vol. 20, 1971, pp. 1313-1319.

Hock et al., "Enantioselective Synthesis of (−)-(19R)-lbogamin-19-ol," Helvetica Chimica Acta, (2006), 89:542-557.

Hodgson et al., "Enantioselective Access to Isoquinuclidines by Tropeone Desymmetrization and Homoallylic Radical Rearrangement: Synthesis of (+)-Ibogamine," Org. Lett., (2005), 26;7(11):2221-2224.

Hoes. "Clinical Criteria for the Selection of Anxiolytics", Tijdschrift voor Therapie Geneesmiddel en Onderzoek, 9:9, 1984, abstract only.

Holbrook. "Nicotine Addiction." In Isselbacher et al. (ed.), "Harrison's Principals of Internal Medicine" 13th Ed., McGraw-Hill Inc., 1994, 2433-2437.

Holzner, et al. "The Neuroleptic Sleeping Course in Chronic Headache", Therapiewoche, 35/36: 1985, abstract only.

Huang, et al. "Cytotoxicity and Sister Chromatid Exchanges Induced in Vitro by Six Anticancer Drugs Developed in the People's Republic of China", Journal of the National Cancer Institute, 71:4, 1983, abstract only.

Hubens, et al. "Chronic Intake of a Hydrogenated Ergot Alkaloid Causing Peripheral Vascular Ischemia—A Case Report", Journal of Vascular Surgery, 21:4, 1987, abstract only.

Huffman, et al. "A Formal Synthesis of (±)-Ibogamine," Journal of Organic Chemistry, vol. 50, 1985, pp. 1460-1464.

(56) References Cited

OTHER PUBLICATIONS

International Search Report and Written Opinion dated Feb. 25, 2013, in related PCT Application No. PCT/US2012/022787.
Isler. "Treatment of Headache", Schweizerische Medizinische Wochenschrift, 114:35, 1984, abstract only.
Jaffe. "Psychopharmacology and Opiate Dependence," U.S. Public Health Services Publication, 1957-1967: pp. 1836.
James. "Linkers for solid phase organic synthesis," Tetrahedron, 55, 1999, pp. 4855-4946.
Jana et al., "Progress in the Synthesis of Iboga-alkaloids and their Congeners," Organic Preparation and Procedures International, (2011), 43:541-573.
Jana et al., "Synthesis of iboga alkaloids by Pd-catalyzed heteroannulation of 2-iodoaniline with an internal alkyne as the key step," Tetrahedron Letters, (2010), 51:1441-1443.
Jane, et al. "High-Performance Liquid Chromatographic Analysis of Basic Drugs on Silica Columns Using Non-Aqueous Ionic Eluents. II. Application of UV, Fluorescence and Electrochemical Oxidation detection", Journal of Chromatography, 323:2, 1985, abstract only.
Jansen, et al. "Ethnopharmacology of Kratom and the Mitragyna Alkaloids", Journal of Ethnopharmacology, 23:1, 1988, abstract only.
Janzen. "History of Use of Psychotropic Drugs in Central Africa," Psychotropes, 1/2: 1983, abstract only.
Justins. "Management strategies for chronic pain," Annals of the Rheumatic Diseases, vol. 55, 1996, pp. 588-596.
Kalix. "Khat: A Plant with Amphetamine Effects," Journal of Substance Abuse Treatment, 5:3, 1988, abstract only.
Kalix. "Pharmacological Properties of the Stimulant Khat", Pharmacological Therapy, 48:3, 1990, abstract only.
Keefner. "A Gas Chromatography-Mass Spectrometry (GCMS) Method for Ibogaine", Society for Neuroscience Abstracts, 19:1-3, 1993, abstract only.
Keller, et al. "Modulation of Neopterin Release by Human Kupffer Cells in Culture: Possible Implication in Clinical Monitoring of HIV-Seropositive Subjects", Cells Hepatic Sinusoid, 3: 1991, abstract only.
Knoll. "Azidomorphines and Homopyrimidazols: A New Approach to the Ideal Analgetic," ACTA Physiologica et Pharmacologica Bulgarica, 3:2, 1977, abstract only.
Knoll. "Azidomorphines: A New Family of Potent Analgesics with Low Dependence Capacity," Progress in Neuro-Psychopharmacology and Biological Psychiatry, 3:1-3, 1979, abstract only.
Koch, et al. "Drug-Induced Liver Injury in Liver Biopsies of the Years 1981 and 1983, their Prevalence and Type of Presentation", Pathology, Research and Practice, 179: 1985, abstract only.
Konig. "Psychiatric Intensive Therapy After Acute Alkaloid Withdrawal Syndrome", Infusionsther Klin Ernahr, 6:1, 1979, abstract only.
Kornetsky. "Pharmacology Drugs Affecting Behavior." John Wiley & Sons, 1976, pp. 185-187.
Kostowski, et al. "The Effects of Some Hallucinogens on Aggressiveness of Mice and Rats" Pharmacology, 7, 1972, pp. 259-263.
Krug. "Cocaine Abuse: Historical, Epidemiologic, and Clinical Perspectives for Pediatricians", Advances in Pediatrics, 36: 1989, pp. 369-406.
Kubiliene, et al., "Acute toxicity of ibogaine and noribogaine," Medicina (Kaunas), (2008), 44(12):984-988.
Kuehne et al., "Biomimetric syntheses of indole alkaloids. 11. Syntheses of .beta.-carboline and indoloazepine intermediates," J. Org. Chem., (1985), 50(7):919-924.
Kupers, et al. "Morphine differentially affects the sensory and affective pain ratings in neuorgenic and idiopathic forms of pain." Pain, 47, 1991, pp. 5-12.
Lakoski, et al. "Electrophysiologic Characterization of an Ibogaine Metabolite in Dorsal Raphe Nucleus and Hippocampus." Society for Neuroscience, 21:716, 1995, abstract only.
Larson-Prior, et al. "Electrophysiologic Characterization of an Ibogaine Metabolite in the Cerebellar Cortex." Society for Neuroscience, 21:716, 1995, abstract only.

Lemontt, et al. "Increase MDR Gene Expression and Decreased Drug Accumulation in Multidrug-Resistant Human Melanoma Cells", Cancer Research, 48:22, 1988, abstract only.
Leoni, et al. "Effect of Cocaine and Morphine on Neutral Endopeptidase Activity of Human Peripheral Blood Mononuclear Cells Cultures with Lectins," Cell Biochemistry and Function, 11:3, 1993, abstract only.
Lerida, et al. "Incidence of Morphine Withdrawal and Quasi-Abstinence Syndrome in a Model of Chronic Pain in the Rat," Neuroscience, 81:1-2, 1987, abstract only.
Lewis, et al. "Adverse Reactions and Interactions with .beta.-Adrenoceptor Blocking Drugs," Journal of Medical Toxicology, 1:5, 1986, abstract only.
Lewis, et al. "Narcotic Analgesics and Antagonists," Annual Review of Pharmacology, 11, 1971, abstract only.
Licht, et al. "Induction of Multiple-Drug Resistance During Anti-Neoplastic Chemotherapy In-Vitro," International Journal of Cancer, 49:4, 1991, abstract only.
Ling, et al. "Drugs of Abuse-Opiates", in Addtiction Medicine [Special Issue], Western Journal of Medicine, 152, 1990, pp. 565-572.
Low, et al. "Effects of Acronycine and Cytouchalasin B on the Division of Rat Leukemia Cells," Experimental Cell Research, 131:1, 1981, abstract only.
Ma, et al. "Inhibition of Respiratory Burst Activity in Alveolar Macrophages by Bisbenzylisoquinoline Alkaloids: Characterization of Drug-Cell Interaction", Experimental Lung Research, 18:6, 1992, abstract only.
Maisonneuve, et al. "Interactions of Ibogaine and D-Amphetamine: in vivio Microdialysis and Motor Behavior in Rats." Brain Research 579, 1992, pp. 87-92.
Maisonneuve, et al. "Acute and Prolonged Effects of Ibogaine on Brain Dopamine Metabolism and Morphine-Induced Locomotor Activity in Rats", Brain Research, 575:1, 1992, abstract only.
Maisonneuve, et al. "Interactions Between Ibogaine, a Potential Anti-Addictive Agent, and Morphine: an in Vivo Microdialysis Study," European Journal of Pharmacology, 199:1, 1991, abstract only.
Martellotta, et al. "Effects of the Calcium Antagonist Isradipine on Cocaine Intravenous Self-Administration in Rats", Psychopharmacologia, 113:3-4, 1994, abstract only.
Martin, et al. "Neuropathic Pain in Cancer Patients: Mechanisms, Syndromes, and Clinical Controversies," Journal of Pain and Symptom Management, 14:2, 1997, pp. 99-117.
Mash, et al. "Ibogaine in the Treatment of Heroin Withdrawal," The Alkaloids 56, 2001, pp. 1-17.
Mash, et al. "Ligand Binding Profiles of Ibogaine and its O-demethylated Metabolite Noribogaine: Implications for Developing Novel Multi-target Anti-addiction Agents." Society of Neurosciences, vol. 21, 1995, abstract only.
Mash, et al. "Preclinical screening of an ibogaie metabolite (noribogaine) on cocaine-induced hyperlocomotion and cocaine self-administration." Society of Neurosciences, vol. 22, 1996, abstract only.
Mash, et al. "Properties of Ibogaine and its Principle Metabolite (12-hydroxyibogamine) at the MK-801 binding site of the NMDA receptor complex," Neuroscience Letters, 192, 1995, pp. 53-56.
Mateer, et al. "Reversible Ipecac Myopathy," Archives of Neurology, 42:2, 1985, abstract only.
Matharu, et al. "Preformulation and Development of Ibogaine Injection for the Treatment of Drug Abuse," Pharmaceutical Research, 10: 1993, abstract only.
Mattingly, et al. "Selective Antagonism of Dopamine D Sub 1 and D Sub 2 Receptors Does Not Block the Development of Behavioral Sensitization to Cocaine," Psychopharmacologia, 114:2, 1994, abstract only.
McNeish, et al. "The 5-HT Sub 3 Antagonist Zacopride Attenuates Cocaine-Induced Increases in Extracellular Dopamine in Rat Nucleus Accumbens," Pharmacology, Biochemistry, and Behavior, 45:4, 1993, abstract only.
Melchior, et al. "Preference for Alcohol Evoked by Tetra Hydro Papaveroline Chronically Infused in the Cerebral Ventricle of the Rat," Pharmacol Biochem Behav, 7:1, 1977, abstract only.

(56) References Cited

OTHER PUBLICATIONS

Mendelson & Mello "Cocaine and Other Commonly Abused Drugs." In Isselbacher et al. (ed.), "Harrison's Principals of Internal Medicine." 13th Ed., McGraw-Hill Inc., 1994, pp. 2429-2433.
Menzies, et al. "Gangrene of the Small Bowel: A Complication of Methysergide Therapy," Australian and New Zealand Journal of Surgery, 52:5, 1982, abstract only.
Metelitsa. "Pharmacological Agents in Controlling Smoking," Biull Vsesoiuznogo Kardiol Nauchn Tsentra, 10:1, 1987, abstract only.
Millan. "k-Opioid Receptors and Analgesia," Trendes in Pharmacologicla Sciences, 11, 1990, pp. 70-76.
Mizuhashi, et al. "Antitumor Activities of IKP-104 A 4-1H Pyridizinone Derivative on Cultured and Implanted Tumors," Japanese Journal of Cancer Research, 81:12, 1990, abstract only.
Moisan et al., "Formal Synthesis of (+)-Catharanthine," Angew. Chem. Int. Ed., (2006), 45:5334-5336.
Montefiori, et al. "In Vitro Evaluation of Mismatched Double-Stranded RNA (Ampligen) for Combination Therapy in the Treatment of Acquired Immunodeficiency Syndrome," AIDS Research and Human Retroviruses, 5:2, 1989, abstract only.
Mulamba, et al. "Alkaloids from Tabernathe Pubescens," Journal of Natural Products, vol. 44:2, 1981, pp. 184-189.
Naranjo. "Ibogaine in psychotherapy: psychoanalysis according to Naranjo", part IV, pp. 1-2. http://www.nettuno.it/fiera/electric.italy/bwitif:html (1969).
Nishiyama, et al. "Expression of the Multidrug Transporter, P-Glycoproteiin, in Renal and Transitional Cell Carcinomas," Cancer, 71:11, 1993, pp. 3611-3619.
Nooter, et al. "Multidrug Resistance (MDR) Genes in Haematological Malignancies," Cytotechnology, 12:1-3, 1993, abstract only.
Nunn-Thompson, et al. "Pharmacotherapy for Making Cessation", Clin Pharm, 8:10, 1989, abstract only.
Obach, et al., "Cythochrome P4502D6 Catalyzes the O-Demethylation of the Psychoactive Alkaloid Ibogaine to 12-Hydroxyibogamine," Drug Metabolism and Disposition 26:8, 1998, pp. 764-768.
O'Hearn, et al. "Degeneration of Prukinje Cells in Parasagittal Zones of the Cerebellar Vermis After Treatment with Ibogaine of Harmaline," Neuroscience, 55:2, 1993, abstract only.
O'Hearn, et al. "Ibogaine Induces Glial Activation in Parasagittal Zones of the Cerebellum," Neuroreport, 4:3, 1993, abstract only.
Pablo, et al, "Noribogaine Stimulates Naloxone-Sensitive[35S]GTPgammaS Binding," NeuroReport, 9, 1998, pp. 109-114. (Website Publication Date of Dec. 20, 1997.).
Pacifici, et al. "Immunological Effect of Cocaine and Host Resistance in Mice," International Journal of Immunotherapy, 8:2, 1992, abstract only.
Palyi. "Survival Responses to New Cytostatic Hexitols of P388 Mouse and K562 Leukemia Cells in Vitro," Cancer Treatment Reports, 70:2, 1986, abstract only.
Pantazis, et al. "Efficacy of Camptothecin Congeners in the Treatment of Human Breast Carcinoma Xenografts," Oncology Research, 5:8, 1994, abstract only.
Paul et al., Synthesis of new series of iboga analogues, Tetrahedron Letters 52(2011) 6166-6169.
PCT International Preliminary Report on Patentability dated Aug. 7, 2014 in PCT Patent Application No. PCT/US2012/022787.
PCT International Search Report and Written Opinion dated May 14, 2013 in related PCT Patent Application No. PCT/US2013/022797.
PCT International Search Report and Written Opinion dated May 31, 2013 in related PCT Patent Application No. PCT/US2013/023017.
Pehek. "Effects of Cathinone and Amphetamine on the Neurochemistry of Dopamine in Vivo," Neuropharmacology, 29:12, 1990, abstract only.
Perera, et al. "Tertiary Indole Alkaloids of Tabernaemontana Dichotoma Seeds," Planta Medica, 49:1, 1983, abstract only.
Perrin. "Clinical Pharmacokinetics of Ergotamine in Migraine and Cluster Headache," Clinical Pharmacokinetics, 10:4, 1985, abstract only.
Popik, et al. "NMDA Antagonist Properties of the pUtative Antiaddictive Drug, Ibogaine," Journal of Pharmaceutical and Experimental Therapeutics, 275:2, 1995, pp. 753-760.
Popik, et al. "The Putative Anti-Addictive Drug Ibogaine is a Competitive Inhibitor of (SUP 3 H) Binding to the NMDA Receptor Complex", Psychopharmacologia, 114:4, 1994, abstract only.
Popik, et al. "100 Years of Ibogaine: Neurochemical and Pharmacological Actions of a Putative anti-addictive Drug," Pharmacological Reviews 47:2, 1995, pp. 235-253.
Pulvirenti, et al. "Lisuride Reduces Intravenous Cocaine Self-Administration in Rats," Pharmacology, Biochemistry and Behavior, 47:4, 1994, abstract only.
Qiu, et al. "The Influence of Chronic Nicotine Treatment on Stress-Induces Gastric Ulceration and Emptying Rate in Rats," Experientia, 48:4, 1992, abstract only.
Radouco-Thomas, et al. "Adverse effects to Psychotomimetics. Proposition of a Psychopharmacological Classification." Pharmacologie, Toxicologie, et abus des psychotomimetiques (hallucinogens), (1974), 109, abstract only.
Rezvani, et al. "Noribogaine, a Primary Ibogaine Metabolite, Reduces Alcohol Intake in P and Fawn-Hooded Rats." RSA Annual Scientific Meeting, 1995, abstract only.
Rezvani, et al. "Reduction of Alcohol Intake in Alcohol Preferring Fawn-hooded and P Rats by Noribogaine, the Primary Metabolite of Ibogaine." NIDA Monograph Series 162:281, 1996, Abstract only.
Ricceri, et al. "Postnatal cocaine Esposure Affects Neonatal Passive Avoidance Performance and Cholinergic Development in Rats," Pharmacology, Biochemistry and Behavior, 45:2, 1993, abstract only.
Rodriguez, et al. "Cocaine Adminstration Prior to Reactivation Facilitates Later Acquisition of an Avoidance Response in Rats," Psychopharmacologia, 112:2-3, 1993, abstract only.
Rosenmund, et al. "Ibogamin, Ibogain and Epiibogamin" Chemische Berichte, 108, 1975, pp. 1871-1895.
Sachs, et al. "Corneal Complications Associated with the Use of Crack Cocaine," Ophthalmology, 100:2, 1993, abstract only.
Salmoiraghi, et al. "Effects of LSD 25, BOL 148, Bufotenine, Mescaline and Ibogaine on the Potentiation of Hexobarbital Hypnosis Produced by Serotonin and Reserpine." Journal of Pharmacology and Experimental Therapeutics 120:1, 1957, pp. 20-25.
Samadi-Baboli, et al. "Preparation of Low Density Lipoprotein-9-Methoxy-Illipticin Complex and Its Cytotoxic Effect Against L1210 and P 388 Leukemic Cells in Vitro," European Journal of Cancer and Clinical Oncology , 25:2, 1989, abstract only.
Saper, et al. "Ergotamine Tartrate Dependency: Features and Possible Mechanisms," Clinical Neuropharmacology, 9:3, 1986, abstract only.
Schecter, et al. "Comparison of the Behavioral Effects of Ibogaine from Three Sources: Mediation of Discriminative Activity," European Journal of Pharmacology, 249:1, 1993, abstract only.
Schneider, et al. "Analysis of the Cardiovascular Action of Ibogaine Hydrochloride." Archives Internationales de Pharmacodynamie et de Thérapie, 110, 1957, pp. 92-102.
Schneider, et al. "Neuropharmacological Studies of Ibogaine: An Indole Alkaloid with Central Stimulant Properties." Annals of the New York Academy of Sciences, 66, 1957, pp. 765-776.
Schneider, et al., "Potentiation Action of Ibogaine on Morphine Analgesia" Experiential, 12, 1956, pp. 323-324.
Schnider, et al. "Use and Abuse of Analgesics in Tension-Type Headache," Cephalalgia, 14:2, 1994, abstract only.
Schuckit & Segal. "Opiod Drug Use." In Isselbacher et al. (ed.), "Harrison's Principals of Internal Medicine" 13th Ed., McGraw-Hill Inc., 1994, 2425-2429.
Schuckit. "Alcohol and Alcoholism," In Isselbacher et al. (ed.), "Harrison's Principals of Internal Medicine." 13th Ed., McGraw-Hill Inc., 1994, pp. 2420-2425.
Seeber, et al. "In Vivo Resistance Towards Anthracyclines, Etoposide, and Cis-Diamminedichloroplatinum (II)," Cancer Research, 42:11, 1982, abstract only.

(56) References Cited

OTHER PUBLICATIONS

Sehested, et al. "The Carboxylic Ionophore Monensin Inhibits Active Drug Efflux and Modulates In-Vitro Resistance in Daunorubicin Resistant Enrlich Ascites Tumor Cells," Biochemical Pharmacology, 37:17, 1988, abstract only.
Sershen, et al. "Ibogaine Antagonizes Cocaine-Induced Locomotor Stimulation in Mice," Life Sciences, 50:15, 1992, abstract only.
Sershen, et al. "Ibogaine Reduces Amphetamine-Induced Locomotor Stimulation in C57BL/6By Mice, but Stimulates Locomotor Activity in Rats," Life Sciences, 51:13, 1992, abstract only.
Sershen, et al. "Ibogaine Reduces Preference for Cocaine Consumption in C57BL/6By Mice," Pharmacology Biochemistry and Behavior, 47:1, 1994, abstract only.
Shen, et al. "Antagonists at Excitatory Opioid Receptors on Sensory Neurons in Culture Increase Potency and Specificity of Opiate Analgesics and Attenuate Development of Tolerance/ Dependence," Brain Research, 636:2, 1994, abstract only.
Sheppard. "A Preliminary Investigation of Ibogaine: Case Reports and Recommendations for Further Study." Journal of Substance Abuse Treatment, 11:4, 1994, abstract only.
Shir, et al. "Neuropathic pain unrelieved by morphine, alleviated by haloperidol," Harefuah 118:8, 1990, abstract only.
Shook, et al. "A Cyclic Somatostatin Analog that Precipitates Withdrawal in Morphine-Dependent Mice," NIDA Residential Monographs, 76, 1987, abstract only.
Sinkula, et al. "Rationale for Design for Biologically Reversible Drug Derivatives: Prodrugs." Journal of Pharmaceutical Sciences, 64:2, 1975, pp. 181-210.
Slotkin, et al. "A Model of Harmine Metabolism in the Rat." The Journal of Pharmacology and Experimental Therapeutics, 174:3, 1970, pp. 456-462.
Slotkin, et al. "Blood Levels and Urinary Excretion of Harmine and its Metabolites in Man and Rats." The Journal of Pharmacology and Experimental Therapeutics, 173:1, 1970, pp. 26-30.
Slotkin, et al. "Urinary Metabolites of Harmine in the Rat and their Inhibition of Monoamine Oxidase." Biochemical Pharmacology, 19, 1970, pp. 125-131.
Sloviter, et al. "A Common Mechanism of Lysergic Acid, Indolealkylamine and Phenethylamine Hallucinogens: Serotonergic Mediation of Behavioral Effects in Rats." Journal of Pharmacological Experimental Therapy, 214:2, 1980, pp. 231-238.
Smith. "Interaction of Biogenic Amines with Ethanol," Advances in Experimental Medicine and Biology, 56, 1975, abstract only.
Solinas, et al. "Solid-Supported Reagents and Catch-and-Release Techniques in Organic Synthesis", Synthesis 2007:16, 2007, pp. 2409-2453.
Stella. "Pro-drugs as Novel Drug Delivery Systems", ed. Higuchi, T. et al., American Chemical Society, Washington D.C., 1975, pp. 1-49.
Stella. "Pro-drugs: An Overview and Definition." Prodrugs as Novel Drug Delivery System. ACS Symposium Series: 1975, pp. 1-115.
Sugiyama, et al. "Quantitative Analysis of Cell-Kill Effects of Anticancer Drugs: Consideration of Both In Vitro and In Vivo Expreimental Systems." Gan To Kagaku Ryoho, 14:12, 1987, abstract only.
Tarnower, et al., "Ergotism Masquerading as Arteritis," Postgradute Medicine, 85:1, 1989, abstract only.
Teoh, et al. "Buprenorphine Effects on Morphine- and Cocaine-Induced Subjective Responses by Drug-Dependent Men," Journal of Clinical Psychopharmacology, 14:1, 1994, abstract only.
Tfelt-Hansen, et al. "Nitroglycerin for Ergotism. Experimental Studies in Vitro and in Migraine Patients and Treatment of an Overt Case," European Journal of Clinical Pharmacology, 22:2, 1982, abstract only.
Torrenegra, et al. "Alkaloids of stemmadenia grandiflora", Phytochemistry, 27:6, 1988, pp. 1843-1848.
Tsuruo. "Multidrug Resistance: A Transport System of Antitumor Agents and Xenobiotics," Princess Takamatsu Symp, 21, 1990, abstract only.
Uldry, et al. "Cerebrovascular Accidents in Relation to Drug Consumption or Drug Abuse," Schweizerische Rundschau Fur Medizin Praxis, 78:23, 1989, abstract only.
Valadez, et al. "Persistence of the Ability of Amphetamine Preexposure to Facilitate Acquistion of Cocaine Self-Administration," Pharmacology, Biochemistry and Behavior, 47:1, 1994, abstract only.
Valencia, et al. "Obovatine, a New Bisindole Alkaloid from Stemmadenia Obovata," Journal of Natural Products, 58:1, 1995, pp. 134-137.
Vescovi, et al. "Successful Treatment of Opiate Withdrawal Using Lysine Acetylsalicylate," Current Therapeutic Research, Clinical and Experimental, 33:5, 1983, abstract only.
Villalba, et al. "Uses and Abuses of Ipecacuana Syrup", Farmacia Clinica, 9:1, 1992, abstract only.
Wells, et al. "Recognition and Treatment of Arterial Insufficiency from Cafergot," Journal of Vascular Surgury, 4:1, 1986, abstract only.
Whitaker, et al. "High Affinity 3H-Serotonin Binding to Caudate: Inhibition by Hallucinogenic and Serotonergic Drugs," Psychopharmacology 59, 1978, pp. 1-5.
Whitaker, et al. "Selective Labeling of Serotonin Receptors by d'(3H)Lysergic Acid Diethylamide in Calf Caudate." Proceedings of the National Academy of Sciences 75:12, 1978, pp. 5783-5787.
White, et al. "Catalyzed Asymmetric Diels-Alder Reactions of Benzoquinone, Total Synthesis of (−)-lbogamine." Helvetica Chimica Acta, 85, 2002, pp. 4306-4327.
Whittaker, et al. "Recurrent Laryngeal Nerve Paralysis in Patients Receiving Vincristine and Vinblastine", British Medical Journal, 1:6071, 1977, abstract only.
Widler, et al. "Pharmacodynamics and Pharmacokinetics of Khat: a Controlled Study," Clinical Pharmacology Therapy, 55:5, 1994, abstract only.
Wildmann. "Heterocycles as Physiological Ligands for the Benzodiazepine Receptor and for Other Binding Sites", Pharmacology Residency, 21:6, 1989, abstract only.
Williams, et al. "The 'Alice in Wonderland' Experience Ergot Alkaloid Therapy for Prolactin-Secreting Pituitary Tumors," The Western Journal of Medicine, 138:3, 1983, abstract only.
Wishart, et al. "Is Multidrug Resistance Relevant in Breast Cancer," European Journal of Surgical Oncology, 17:5, 1991, abstract only.
Witt, et al. "Pharmacodynamic and Pharmacokinetic Characterization of Poly(Ethylene glycol) Conjugation to Met-Enkephalin Analog [D-Pen2,D-Pen5]-enkephalin (DPDPE)", Journal of Pharmcological and Experimental Therapy, 298:2, 2001, pp. 848-856.
Witt, et al. "Pluronic P85 Block Copolymer Enhances Opioid Pepetide Analgesia," Journal of Pharmcology and Experimental Therapy, 303:2, 2002, pp. 760-767.
Worz. "Effects and Risks of Psychotropic and Analgesic Combinations," American Journal of Medicine, 75:5A, 1983, abstract only.
Zetler, et al. "Pharmacokinetics in the Rat of the Hallucinogenic Alkaloids Harmine and Harmaline." Naunyn-Schmiedeberg's Archives of Pharmacology, 285, 1974, pp. 273-292.
Zetler, et al. "Cerebral Pharmacokinetics of Tremor-Producing Harmala and Iboga Alkaloids" Pharmacology, 7:4, 1972, pp. 237-248.
Duranti et al., "2-Bromomelatonin: synthesis and characterization of a potent melatonin agonist," Life Sciences, 1992, vol. 51, No. 7, pp. 479-485.
International Search Report and Written Opinion issued on PCT/US2015/036045, mailed Mar. 31, 2016.
Jana, G.K. et al., "Total synthesis of ibogaine, epiibogaine and their analogues", Tetrahedron, 2012, vol. 68. No. 35, pp. 7155-7165.
Chemical Abstract compounds, STN express, RN 663195-14-0 Registry (entered STN: Mar. 15, 2014) and 345230-12-8 (Entered STN: Jul. 10, 2001).

\* cited by examiner

HALOGENATED INDOLE AND BENZOFURAN DERIVATIVES OF ISOQUINUCLIDENE AND PROCESSES FOR PREPARING THEM

CROSS-REFERENCE TO PRIORITY APPLICATIONS

This application claims priority under 35 U.S.C. §119(e) to U.S. Provisional Patent Application Ser. No. 62/013,771, filed on Jun. 18, 2014, which is incorporated herein by reference in its entirety.

FIELD OF THE INVENTION

Provided herein are halogenated indole and benzofuran derivatives of isoquinuclidene and intermediates thereto, and processes, preferably enantioselective processes, for preparing such derivatives including processes for preparing (−) and (+) noribogaine, in substantially enantiomerically pure forms.

STATE OF THE ART

Noribogaine is a well-known compound whose structure combines the features, for example, of tyrptamine, and isoquinuclidene. The naturally occurring enantiomer of noribogaine can be depicted by the following formula:

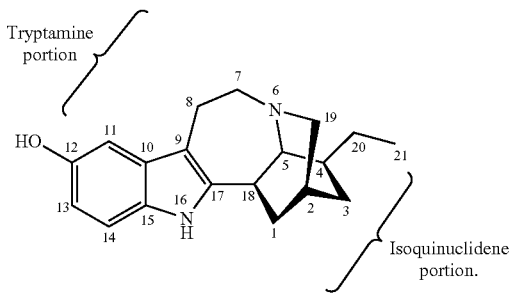

This enantiomer of noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737). Both of these patents are incorporated herein by reference in their entirety.

Synthesizing compounds to include the isoquinuclidene moiety, especially in a substantially enantiomerically pure form is a challenging task. Heretofore, Iboga alkaloids, such as ibogaine:

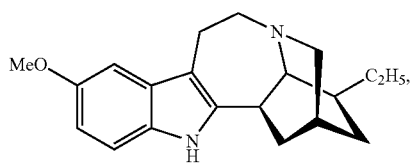

were conventionally prepared from one of its naturally occurring precursors such as voacangine:

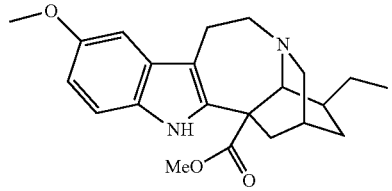 [SMILES: CCC1CC2CN3CCc4c([nH]c5ccc(OC)cc45)C(C(=O)OC)(C2)C13]

or isolated from plant sources. The naturally occurring enantiomer of noribogaine is prepared by O-demethylation of naturally occurring ibogaine or prepared by decarboxylation and O-demethylation of naturally occurring voacangine. Voacangine and Ibogaine are obtained from plants where both the supply is limited and the quality of the supply is unpredictable.

SUMMARY OF THE INVENTION

Provided herein are halogenated indole and benzofuran derivatives of isoquinuclidene and intermediates thereto, and processes, preferably enantioselective processes, for preparing such derivatives including processes for preparing (−) and (+) noribogaine, in substantially enantiomerically pure forms. Also provided herein are intermediates and processes for preparing noribogaine following the Nenitzescu indole synthesis.

DETAILED DESCRIPTION OF THE INVENTION

Before this invention is described in greater detail, the following terms will be defined.

DEFINITIONS

As used herein and in the appended claims, the singular forms "a", "an", and "the" include plural referents unless the context clearly dictates otherwise. Thus, for example, reference to "a salt" includes a plurality of such salts.

As used herein, "alkenyl" refers to hydrocarbyl groups having from 2 to 10 carbon atoms and at least one and up to 3 carbon carbon double bonds. Examples of alkenyl include vinyl, allyl, dimethyl allyl, and the like.

As used herein, "alkoxy" refers to —O-alkyl.

As used herein, "alkyl" refers to hydrocarbyl groups having from 1 to 10 carbon atoms, more preferably 1 to 6 carbon atoms, and still more preferably 1-4 carbon atoms. The alkyl group may contain linear or branched carbon chains. This term is exemplified by groups such as methyl, ethyl, n-propyl, iso-propyl, n-butyl, t-butyl, n-pentyl, n-decyl and the like.

As used herein, "alkynyl" refers to hydrocarbyl groups having from 2 to 10 carbon atoms and at least one and up to 2 carbon carbon triple bonds. Examples of alkynyl include ethynyl, propargyl, dimethylpropargyl, and the like.

As used herein, "under amide formation conditions" refers to conditions, as is well known to the skilled artisan, under which a —$CO_2H$ group or a —CO-$L^1$ group, wherein $L^1$ is a leaving group reacts with an amine to form an amide. A —$COL^1$ moiety can react with a suitable amine in the presence of a base, and optionally a nucleophilic catalyst such as N,N-dimethylamino pyridine or the likes, in an inert solvent such as dichloromethane, tetrahydrofuran, or the likes. Suitable bases include triethyl amine, pyridine, and well known modifications of each thereof. A $CO_2H$ moiety reacts with a suitable amine in the presence of a reagent such as a carbodiimide or a variety of such reagents well known in chemistry and peptide chemistry.

As used herein, "amino" refers to —NR$^x$R$^y$ wherein each R$^x$ and R$^y$ independently is hydrogen, $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heteroaryl, or $C_3$-$C_8$ heterocyclyl, or R$^x$ and R$^y$ together with the nitrogen atom they are bonded to form a 5-10 membered heterocyclyl ring containing 1-2 nitrogen and/or oxygen atoms, which heterocyclyl ring is optionally substituted with 1-3, preferably, 1-2, or more preferably, a single, $C_1$-$C_3$ alkyl group.

As used herein, "aryl" refers to an aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom.

As used herein, "base" refers to a compound that can accept a proton or donate a lone electron pair. Examples of bases include, alkali (Oft), carbonate, bicarbonate, alkoxides (alkyl-On), hydrides (alkali metal hydrides and $CaH_2$), amides ($NH_2$(−), $R^b$NH(−), or ($R^b$)$_2$N(−), wherein $R^b$ is alkyl or 2 $R^b$s together with the nitrogen form a 5-6 membered ring), and neutral nitrogen containing bases such as ($R^b$)$_3$N, pyridine, 4-N,N-dialkylpyridine, and the like. As used herein nucleophilic bases refer to preferably neutral nitrogen containing bases that can catalyze the addition of an acyl halide or a sulfonyl halide(such as $R^b$COX or $R^b$SO$_2$X) to an —OH, —NH$_2$, or an —NHR$^b$ group. Preferred examples include, 4-N,N-dialkylpyridines.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, "a condition suitable for reductive Heck coupling" refers to a Heck coupling reaction condition where a β-hydride elimination is limited or is not possible. A Heck coupling, including obvious variants thereof, are well known to the skilled artisan. The reaction scheme below illustrates, without limitation, a reaction condition where a reductive Heck reaction takes place.

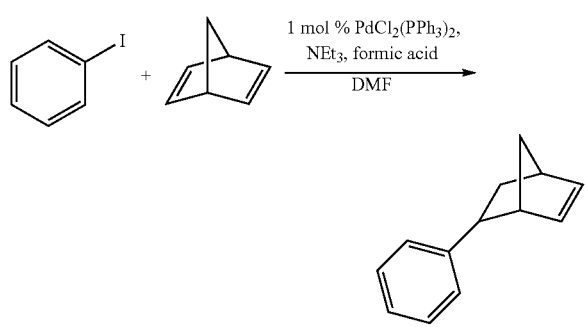

For example, a reaction may take place with a suitable hydride donor. In that case, a Heck reaction is carried out on a substrate which will not allow β-hydride elimination. The addition, for example, of formic acid or ammonium formate leads to a σ-alkyl palladium intermediate and causes a "reductive Heck" reaction.

As used herein, "cycloalkyl" refers to cyclic hydrocarbyl groups of from 3 to 10 carbon atoms having single or multiple condensed rings, which condensed rings may be aromatic or contain a heteroatom, provided that the point of attachment is at a cycloalkyl carbon atom. Cycloalkyl includes, by way of example, adamantyl, cyclopropyl, cyclobutyl, cyclopentyl, cyclooctyl and the like. Cycloalkyl rings are preferably saturated, though, cycloalkyl rings including 1-2 carbon carbon double bonds are also contemplated provided that the ring is not aromatic.

As used herein, "$C_x$" refers to a group having x carbon atoms, wherein x is an integer, for example, $C_4$ alkyl refers to an alkyl group having 4 carbon atoms.

As used herein, "ee" refers to enantiomeric excess and is expressed as $(e^1-e^2)\%$ where $e^1$ and $e^2$ are the two enantiomers. For example, if the % of $e^1$ is 95 and the % of $e^2$ is 5, then the $e^1$ enantiomer is present in an ee of 90%. The ee of an enantiomer in a mixture of enantiomers is determined following various methods well known to the skilled artisan, such as using chiral lanthanide based nuclear magnetic resonance shift reagents, forming derivatives with chiral compounds such as chiral hydroxyacids, amino acids, and the like. Various physical measurements such as circular dichroism, optical rotation, etc. are also useful in determining the ee of a mixture of enantiomers.

As used herein, —CO$_2$H "ester" refers to —CO$_2$R$^E$ wherein R$^E$ is selected from the group consisting of $C_6$-$C_{10}$ aryl and $C_1$-$C_6$ alkyl optionally substituted with 1-3 $C_6$-$C_{10}$ aryl groups.

As used herein, "halo" refers to F, Cl, Br, or I.

As used herein, "halogenating agent" refers to a compound that can convert an indole, to a 2-halo indole. Non-limiting examples of such reagents include N-halosuccinimides such as N-iodosuccinimide. Conditions suitable for halogenation include contacting the reactants in an inert solvent.

As used herein, "heteroaryl" refers to an aromatic group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—), provided that the ring has at least 5 ring atoms and up to 14, or preferably from 5-10, ring atoms. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Examples of heteroaryls include pyridyl, pyrrolyl, indolyl, thiophenyl, furyl, and the like.

As used herein, "heterocyclyl" or heterocycle refers to a cycloalkyl group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—), provided that the ring has at least 3 and up to 14, or preferably from 5-10 ring atoms. Such heterocyclyl groups can have a single ring or multiple condensed rings wherein the condensed rings may not contain a heteroatom and/or may contain an aryl or a heteroaryl moiety, provided that the point of attachment is through an atom of the non-aromatic heterocyclyl group. Examples of heterocyclyl include pyrrolidinyl, piperadinyl, piperazinyl, and the like. Heterocyclyl rings are preferably saturated, though, heterocyclyl rings including 1-2 carbon carbon double bonds are also contemplated provided that the ring is not aromatic.

As used herein, "hydrogenation conditions" refer to conditions including hydrogen gas at atmospheric or higher pressure and catalysts that catalyze the reaction of the hydrogen with a hydrogen reactive group, such as a benzyl group or a carbon carbon double/triple bond. Catalysts useful for hydrogenation include palladium, platinum, and rhodium metals and their oxides or hydroxides, preferably supported on a material such as carbon or alumina.

As used herein, "leaving group" refers to a group or an atom that can be displaced by a nucleophile such as an amine. Non-limiting examples of leaving groups include halo, preferably, chloro, bromo, or iodo, and —OSO$_2$R$^{60}$ wherein R$^{60}$ is is $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, or is $C_3$-$C_8$ heterocyclyl, $C_6$-$C_{10}$ aryl, $C_3$-$C_8$ cycloalkyl, $C_2$-$C_{10}$ heteroaryl, or $C_3$-$C_8$ heterocyclyl; wherein the cycloalkyl, heterocyclyl, aryl, or heteroaryl, is optionally substituted with 1-3 substituents selected from the group consisting of $C_1$-$C_6$ alkyl, $C_2$-$C_6$ alkenyl, $C_2$-$C_6$ alkynyl, $C_6$-$C_{10}$ aryl, cycloalkyl, $C_2$-$C_{10}$ heteroaryl, $C_3$-$C_8$ heterocyclyl, halo, or $C_1$-$C_6$ alkoxy.

As used herein, "nucleophilic substitution conditions" refer to those suitable for a nucleophilic substitution at an aliphatic saturated carbon atom, with a nucleophile such as an amine. The reaction are carried out preferably in an aprotic solvent. A non-nucleophilic base, e.g., a base that does not compete with the reacting amine as a nucleophile, such as $K_2CO_3$ may be employed to neutralize any acid generated in the process.

As used herein, "protecting group" or "Pg" refers to well known functional groups which, when bound to a functional group, render the resulting protected functional group inert to the reaction to be conducted on other portions of the compound and the corresponding reaction condition, and which can be reacted to regenerate the original functionality under deprotection conditions. The protecting group is selected to be compatible with the remainder of the molecule. In one embodiment, the protecting group is an "amine protecting group" which protects an —NH— or an —NH$_2$— moiety, for example during the syntheses described here. Examples of amine protecting groups include, for instance, benzyl, acetyl, oxyacetyl, carbonyloxybenzyl (Cbz), Fmoc, and the like. In another embodiment, the protecting group is a "hydroxy protecting group" which protects a hydroxyl functionality during the synthesis described here. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, and benzyl. As the skilled artisan would appreciate, one or more of these protecting groups are also useful as amine protecting groups. Additional examples of amine, hydroxy, and keto protecting groups are found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting hydroxyl, —NH—, —NH$_2$—, and keto groups disclosed herein can be found in the art, and specifically in Greene and Wuts, supra, and the references cited therein.

As used herein, "reducing agent" refers to a compounds that can donate electrons or a hydride in a reaction. Preferred examples include aluminum hydrides, such as LiAlH$_4$, borohydrides such as NaBH$_4$/CeCl$_3$, and alanes such as diisobutyl aluminum hydride. A reducing agent reduces under reduction conditions. Typically the reducing agent and the compound to be reduced, such as a keto-containing compound is reacted in an inert solvent such as ether, tetrahydrofuran, or dioxane. The reaction mixture can be refluxed.

As used herein, a salt refers to preferably a salt of a mineral acid, or an organic acid such as a carboxylic acid or a sulfonic acid, and/or to alkali, alkaline earth, and various ammonium (including tetraalkyl ammonium, pyridinum, imidazolium and the like) salts. Non limiting examples of acid salts include salts of hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, and citric acid.

As used herein, "substantially enantiomerically enriched," "substantially enantiomerically pure" or "substantial enantiomeric excess" or grammatical equivalents thereof refers to an enantiomer in an enantiomeric mixture with at least 95% ee, preferably 98% ee, or more preferably 99% ee.

Compounds

In one aspect, provided herein is a compound of Formula (I):

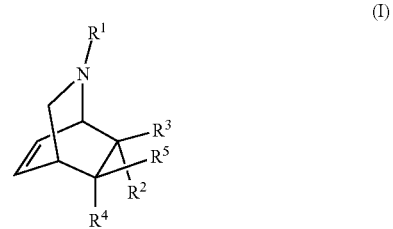

or a tautomer thereof or a salt of each thereof wherein
R$^1$ is selected from the group consisting of hydrogen, —CO$_2$R$^{11}$, —COR$^{12}$, —C(R$^{13}$)$_3$, an amine protecting group, and

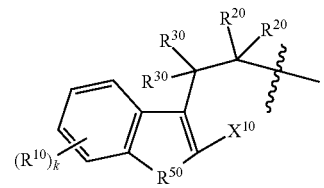

R$^{11}$ is selected from the group consisting of $C_1$-$C_6$ alkyl optionally substituted with 1-3 substituents selected from $C_6$-$C_{10}$ aryl, $C_3$-$C_8$ cycloalkyl, $C_2$-$C_{10}$ heteroaryl, $C_3$-$C_8$ heterocyclyl, halo, amino, —N$_3$, hydroxy, $C_1$-$C_6$ alkoxy, silyl, nitro, cyano, and CO$_2$H or an ester thereof, $C_2$-$C_6$ alkenyl, $C_2$-$C_6$ alkynyl, $C_6$-$C_{10}$ aryl, $C_2$-$C_{10}$ heteroaryl, $C_3$-$C_8$ cycloalkyl, and $C_3$-$C_8$ heterocyclyl, R$^{12}$ and R$^{13}$ independently are selected from the group consisting of hydrogen, $C_1$-$C_6$ alkyl optionally substituted with 1-3 substituents selected from $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof, $C_2$-$C_6$ alkenyl, $C_2$-$C_6$ alkynyl, $C_6$-$C_{10}$ aryl, $C_2$-$C_{10}$ heteroaryl, $C_3$-$C_8$ cycloalkyl, and $C_3$-$C_8$ heterocyclyl;

k is 0, 1, 2, or 3;

each $R^{10}$ is independently a substituent (i.e., when k is 0, the indole moiety includes 4 hydrogens in the phenyl portion) selected from the group consisting of halo, amino, hydroxy, $C_1$-$C_6$ alkoxy, $C_1$-$C_6$ alkyl, $C_2$-$C_6$ alkenyl, $C_2$-$C_6$ alkynyl, cyano, nitro, —$N_3$, and —$CO_2H$ or an ester thereof, wherein the alkyl, alkoxy, alkenyl, or the alkylnyl group is optionally substituted with 1-3 substituents selected from the group consisting of keto, halo, amino, hydroxy, cyano, nitro, —$N_3$, phenyl optionally substituted with 1-3 substituents selected from the group consisting of $C_1$-$C_6$ alkyl and $C_1$-$C_6$ alkoxy, and —$CO_2H$ or an ester thereof;

$R^{20}$ is hydrogen or $C(R^{20})_2$ is a keto group;

$R^{30}$ is selected from the group consisting of hydrogen, halo, $C_1$-$C_6$ alkyl, $C_2$-$C_6$ alkenyl, $C_2$-$C_6$ alkynyl, wherein the alkyl, alkenyl, or the alkylnyl group is optionally substituted with 1-3 substituents selected from the group consisting of keto, halo, amino, hydroxy, cyano, nitro, —$N_3$, and —$CO_2H$ or an ester thereof;

$R^{50}$ is selected from the group consisting of —O— and N—$R^{51}$; and $R^{51}$ is selected from the group consisting of hydrogen and $C_1$-$C_6$ alkyl optionally substituted with 1-3 substituents selected from the group consisting of keto, halo, amino, hydroxy, cyano, nitro, —$N_3$, and —$CO_2H$ or an ester thereof;

$X^{10}$ is a leaving group, preferably, halo or —$OSO_2R^{71}$, more preferably bromo or iodo, or is —OH or hydrogen;

$R^4$ and $R^5$ independently are selected from the group consisting of hydrogen, halo, $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, vinyl, ethynyl, and $CO_2H$ or an ester thereof;

$R^2$ and $R^3$ are independently selected from hydrogen, —CHO, $R^6$—C(=O)—, $R^6$—CH($OR^7$)—, provided that at least one of $R^2$ and $R^3$ is hydrogen; or $R^2$ and $R^3$ together with the carbon atom they are bonded to, form a =$CHR^6$ moiety;

$R^6$ is $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, or $C_3$-$C_8$ heterocyclyl;

$R^7$ is hydrogen or $SO_2R^{71}$;

$R^{71}$ is $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, or is $C_3$-$C_8$ heterocyclyl, $C_6$-$C_{10}$ aryl, $C_3$-$C_8$ cycloalkyl, $C_2$-$C_{10}$ heteroaryl, or $C_3$-$C_8$ heterocyclyl;

wherein the cycloalkyl, heterocyclyl, aryl, or heteroaryl, is optionally substituted with 1-3 substituents selected from the group consisting of $C_1$-$C_6$ alkyl, $C_2$-$C_6$ alkenyl, $C_2$-$C_6$ alkynyl, $C_6$-$C_{10}$ aryl, cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof.

A keto substituent, as used herein, substitutes a —$CH_2$— group to a —C(=O)-group. In one embodiment, $X^{10}$ is a leaving group, preferably, halo or —$OSO_2R^{71}$, more preferably bromo or iodo, or is —OH. In one embodiment, $X^{10}$ is more preferably, halo In one embodiment, the compound is of Formula (II):

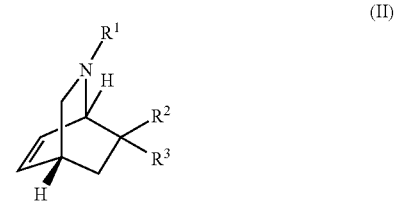

(II)

wherein $R^1$, $R^2$, and $R^3$ are defined as above.

In another embodiment, $R^1$ is hydrogen or $CO_2R^{11}$ and $R^{11}$ is $C_1$-$C_6$ alkyl.

In another embodiment, provided herein is a compound of Formula (III):

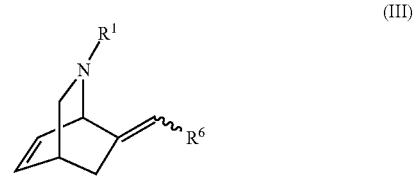

(III)

wherein ⁓ refers to a cis or a trans stereochemistry and $R^1$ is defined as in any aspect or embodiment herein.

In another embodiment, one of $R^2$ and $R^3$ is hydrogen, and the other is —CHO, $COCH_3$, $CHOHCH_3$, —$CHOSO_2R^{71}$ wherein $R^{71}$ is defined as herein.

In another embodiment, provide herein is a compound of Formula (IV):

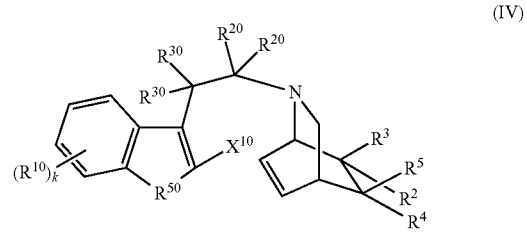

(IV)

wherein the variables are defined as in any aspect or embodiment herein.

In another embodiment, provided herein is a compound of Formula (IVA):

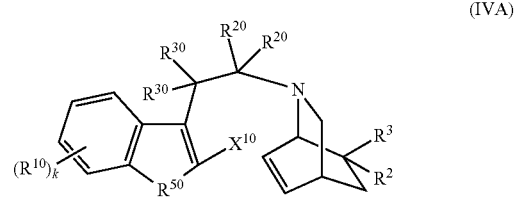

(IVA)

wherein the variables are defined as in any aspect and embodiment above.

In another embodiment, provided herein is a compound of Formula (IVB):

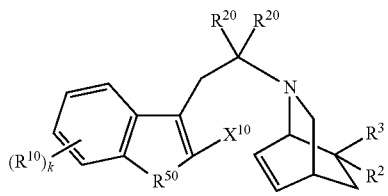

(IVB)

wherein the variables are defined as in any aspect or embodiment above.

In another embodiment, provided herein is a compound of Formula (IVC):

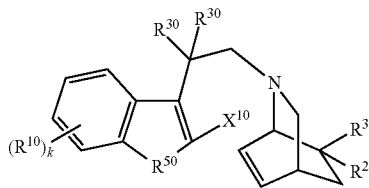

(IVC)

wherein the variables are defined as in any aspect or embodiment above.

In another embodiment, provided herein is a compound of Formula (VA):

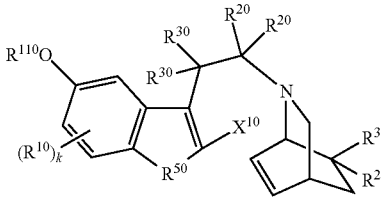

(VA)

wherein $R^{110}$ is selected from the group consisting of
hydrogen;
$C_1$-$C_6$ alkyl optionally substituted with 1-3 substituents selected from the group consisting of halo, amino, hydroxy, cyano, nitro, $-N_3$, $-CO_2H$ or an ester thereof, and phenyl optionally substituted with 1-3 substituents selected from the group consisting of $C_1$-$C_6$ alkyl and $C_1$-$C_6$ alkoxy;
$-COR^{11}$; and
$-CO_2R^{11}$;
k is 0, 1 or 2;
and the remaining variables are defined as in any aspect and embodiment herein.

In another embodiment, provided herein is a compound of Formula (VB):

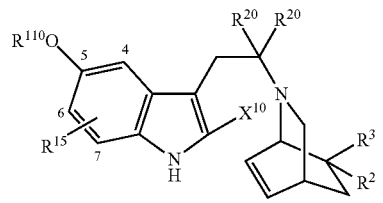

(VB)

wherein the variables are as tabulated below:

| $R^{15}$ | $R^{110}$ | $C(R^{20})_2$ | $R^2$ | $R^3$ | $R^{47}$ |
|---|---|---|---|---|---|
| H, 4-Me, 6-Me, 7-Me, 4-OH, 6-OH, 7-OH, 4-OMe, 6-OMe, or 7-OMe | Bn | C=O | $CR^2R^3$ is $C=CR^{48}H$, $R^{48}$ is Me, Et, Pr, Bu | — | — |
| H, 4-Me, 6-Me, 7-Me, 4-OH, 6-OH, 7-OH, 4-OMe, 6-OMe, or 7-OMe | Bn | $CH_2$ | $CR^2R^3$ is $C=CR^{48}H$, $R^{48}$ is Me, Et, Pr, Bu | — | — |
| H, 4-Me, 6-Me, 7-Me, 4-OH, 6-OH, 7-OH, 4-OMe, 6-OMe, or 7-OMe | Bn | C=O | $CH_2CH_2R^{47}$ | H | $C_1$—$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., 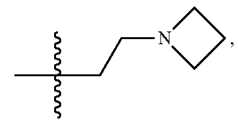 [SMILES: *CCN1CCC1], |

-continued

| $R^{15}$ | $R^{110}$ | $C(R^{20})_2$ | $R^2$ | $R^3$ | $R^{47}$ |
|---|---|---|---|---|---|
| | | | | | 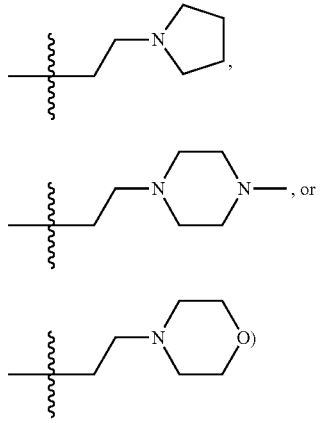 |
| H, 4-Me, 6-Me, 7-Me, 4-OH, 6-OH, 7-OH, 4-OMe, 6-OMe, or 7-OMe | Bn | $CH_2$ | $CH_2CH_2R^{47}$ | H | $C_1$—$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 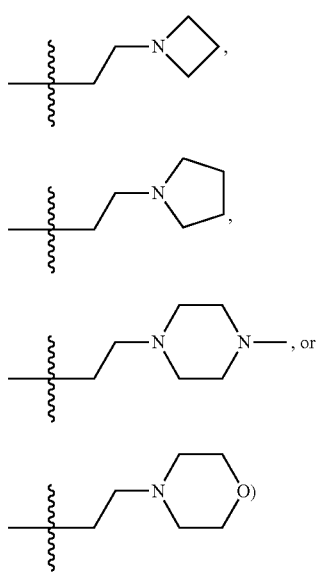 |
| H, 4-Me, 6-Me, 7-Me, 4-OH, 6-OH, 7-OH, 4-OMe, 6-OMe, or 7-OMe | H | C=O | $CH_2CH_2R^{47}$ | H | $C_1$—$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, |

-continued
| $R^{15}$ | $R^{110}$ | $C(R^{20})_2$ | $R^2$ | $R^3$ | $R^{47}$ |
|---|---|---|---|---|---|
| | | | | | 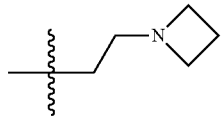 |
| | | | | | 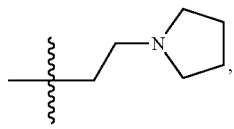 [SMILES: *CCN1CCCC1] |
| | | | | | 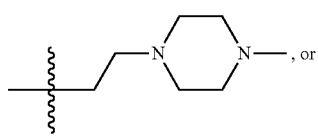 [SMILES: *CCN1CCN(C)CC1] |
| | | | | | 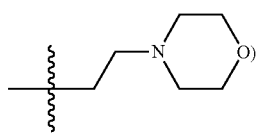 |
| H, 4-Me, 6-Me, 7-Me, 4-OH, 6-OH, 7-OH, 4-OMe, 6-OMe, or 7-OMe | H | $CH_2$ | $CH_2CH_2R^{47}$ | H | $C_1$—$C_4$ alkyl (e.g., Me, Et, Pr, Bu) optionally substituted with an OMe group (e.g., $CH_2OMe$, $(CH_2)_2OMe$, $(CH_2)_3OMe$, and $(CH_2)_4OMe$), OH group (e.g., $CH_2OH$, $(CH_2)_2OH$, $(CH_2)_3OH$, and $(CH_2)_4OH$), an amide (e.g., $(CH_2)_2NHCOMe$, $(CH_2)_3NHCOMe$, and $(CH_2)_4NHCCOMe$) or with an amino group (e.g., $CO_2(CH_2)_2NMe_2$, 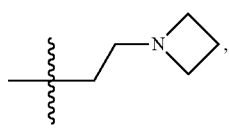 [SMILES: *CCN1CCC1] 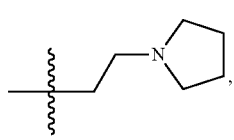 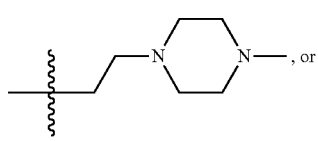 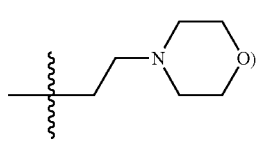 |

In another embodiment, provided herein is a compound of formula;

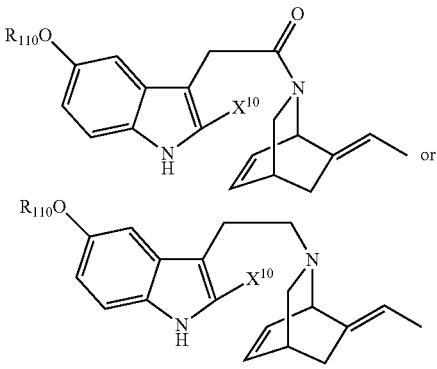

wherein $X^{10}$ is hydrogen, chloro, bromo, or iodo and $R^{110}$ is defined as in any aspect and embodiment above.

In one embodiment, $R^4$, $R^5$, $R^{20}$, and $R^{30}$ are hydrogen.

In another embodiment, $R^{50}$ is $NR^{51}$. In one embodiment, $R^{50}$ is NH. In another embodiment, $R^{50}$ is O.

In another embodiment, $CR^2R^3$ is =CHMe.

In another embodiment, k is 0. In another embodiment, k is 0 and preferably, the phenyl ring is substituted with the —O—$R^{110}$ group. In another embodiment, $R^{110}$ is $C_1$-$C_6$ alkyl optionally substituted with 1-3 substituents selected from phenyl optionally substituted with 1-3 substituents selected from the group consisting of $C_1$-$C_6$ alkyl and $C_1$-$C_6$ alkoxy.

Preparation

Cyclization e.g., by Reductive Heck Coupling

In another aspect, provided herein is a process of preparing a compound of Formula (VI):

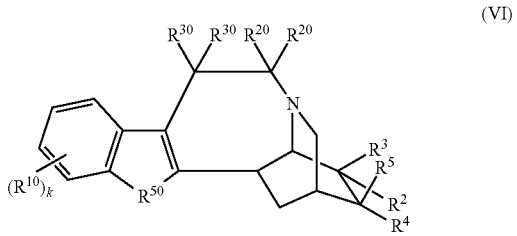

or a tautomer thereof or a salt of each thereof wherein k is 0, 1, 2, or 3;

each $R^{10}$ is independently a substituent selected from the group consisting of halo, amino, hydroxy, $C_1$-$C_6$ alkoxy, $C_1$-$C_6$ alkyl, $C_2$-$C_6$ alkenyl, $C_2$-$C_6$ alkynyl, cyano, nitro, —$N_3$, and —$CO_2H$ or an ester thereof, wherein the alkyl, alkoxy, alkenyl, or the alkylnyl group is optionally substituted with 1-3 substituents selected from the group consisting of keto, halo, amino, hydroxy, cyano, nitro, —$N_3$, phenyl optionally substituted with 1-3 substituents selected from the group consisting of $C_1$-$C_6$ alkyl and $C_1$-$C_6$ alkoxy, and —$CO_2H$ or an ester thereof;

$R^{20}$ is hydrogen or $C(R^{20})_2$ is a keto group;

$R^{30}$ is selected from the group consisting of hydrogen, halo, $C_1$-$C_6$ alkyl, $C_2$-$C_6$ alkenyl, $C_2$-$C_6$ alkynyl, wherein the alkyl, alkenyl, or the alkylnyl group is optionally substituted with 1-3 substituents selected from the group consisting of keto, halo, amino, hydroxy, cyano, nitro, —$N_3$, and —$CO_2H$ or an ester thereof;

$R^{50}$ is selected from the group consisting of —O— and N—$R^{51}$; and $R^{51}$ is selected from the group consisting of hydrogen and $C_1$-$C_6$ alkyl optionally substituted with 1-3 substituents selected from the group consisting of keto, halo, amino, hydroxy, cyano, nitro, —$N_3$, and —$CO_2H$ or an ester thereof;

$R^4$ and $R^5$ independently are selected from the group consisting of hydrogen, halo, $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, vinyl, ethynyl, and $CO_2H$ or an ester thereof;

$R^2$ and $R^3$ are independently selected from hydrogen, —CHO, $R^6$—C(=O)—, $R^6$—CH(O$R^7$)—, provided that at least one of $R^2$ and $R^3$ is hydrogen; or $R^2$ and $R^3$ together with the carbon atom they are bonded to, form a =CH$R^6$ moiety;

$R^6$ is $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, or $C_3$-$C_8$ heterocyclyl;

$R^7$ is hydrogen or $SO_2R^{71}$;

$R^{71}$ is $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, or is $C_3$-$C_8$ heterocyclyl, $C_6$-$C_{10}$ aryl, $C_3$-$C_8$ cycloalkyl, $C_2$-$C_{10}$ heteroaryl, or $C_3$-$C_8$ heterocyclyl;

wherein the cycloalkyl, heterocyclyl, aryl, or heteroaryl, is optionally substituted with 1-3 substituents selected from the group consisting of $C_1$-$C_6$ alkyl, $C_2$-$C_6$ alkenyl, $C_2$-$C_6$ alkynyl, $C_6$-$C_{10}$ aryl, cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof;

the process comprising subjecting a compound of Formula (IV):

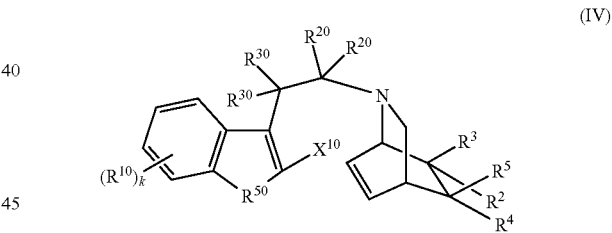

wherein $X^{10}$ is a leaving group, preferably, halo or —$OSO_2R^{71}$, more preferably bromo or iodo and the remaining variables are defined as above, e.g., for Formula (VI);

to a condition suitable for reductive Heck coupling to provide the compound of Formula (VI).

In one embodiment, the compound prepared is of Formula (VIA):

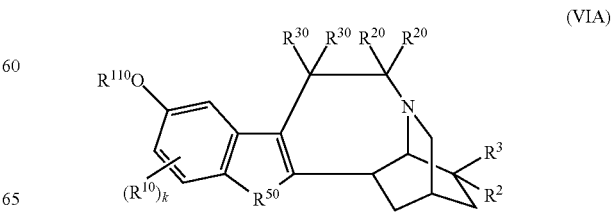

wherein $R^{110}$ is selected from the group consisting of
hydrogen;

$C_1$-$C_6$ alkyl optionally substituted with 1-3 substituents selected from the group consisting of halo, amino, hydroxy, cyano, nitro, —$N_3$, —$CO_2H$ or an ester thereof, and phenyl optionally substituted with 1-3 substituents selected from the group consisting of $C_1$-$C_6$ alkyl and $C_1$-$C_6$ alkoxy;

—$COR^{11}$; and

—$CO_2R^{11}$;

k is 0, 1 or 2;

and the remaining variables are defined as in any aspect and embodiment above, wherein the compound of Formula (VIA) is prepared comprising subjecting a compound of Formula (VA):

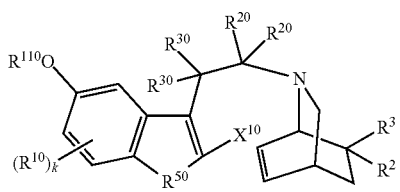

(VA)

wherein $X^{10}$ is halo, preferably, bromo or iodo, more preferably, iodo, to a condition suitable for reductive Heck coupling to provide the compound of Formula (VIA).

Amide and Amine Formation

In one aspect, provided herein is a process of preparing a compound of formula (IV):

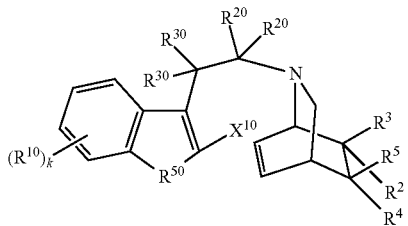

(IV)

wherein $X^{10}$ is a leaving group, $C(R^{20})_2$ is C=O, and the remaining variables are as defined herein, such as above, is prepared comprising contacting a compound of Formula (VIIIC):

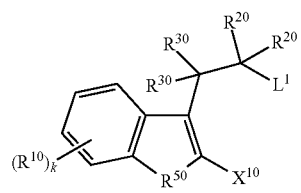

(VIIIC)

wherein $L^1$ is OH or another leaving group selected from halo, preferably chloro or bromo with a compound of Formula (IX):

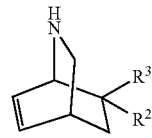

(IX)

under amide formation conditions to prepare the compound of Formula (IV); or wherein the compound of Formula (VIIC):

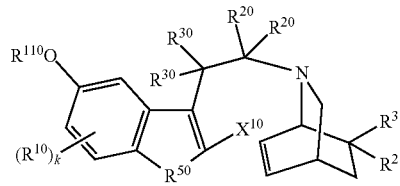

(VIIC)

wherein $C(R^{20})_2$ is C=O and the remaining variables are as defined herein, such as above, is prepared comprising contacting a compound of Formula (VIIID)

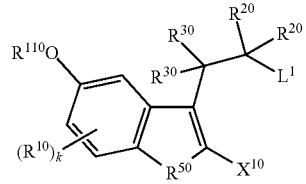

(VIIID)

wherein $L^1$ is OH or another leaving group selected from halo, preferably chloro or bromo with a compound of Formula (IX):

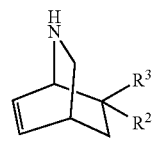

(IX)

under amide formation conditions to prepare the compound of Formula (VIIC).

In one aspect, provided herein is a process of preparing a compound of formula (IV):

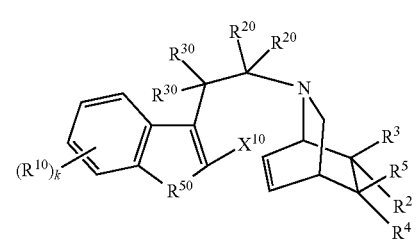

(IV)

wherein $X^{10}$ is a leaving group and $C(R^{20})_2$ is $CH_2$ is prepared comprising contacting a compound of Formula (VIIIC):

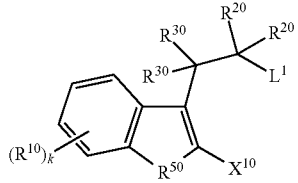
(VIIIC)

wherein $L^1$ is a leaving group with a compound of Formula (IX):

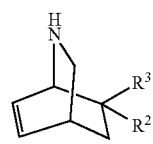
(IX)

under nucleophilic substitution conditions to prepare the compound of Formula (IV); or
wherein the compound of Formula (VIIC):

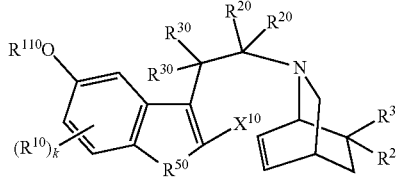
(VIIC)

wherein $C(R^{20})_2$ is $CH_2$ is prepared comprising contacting a compound of Formula (VIIID)

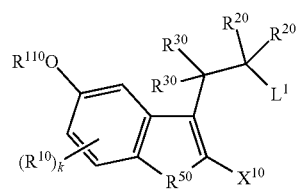
(VIIID)

wherein $L^1$ is a leaving group with a compound of Formula (IX):

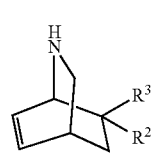
(IX)

under nucleophilic substitution conditions to prepare the compound of Formula (VIIC).

In another embodiment, provided herein a process for preparing a compound of Formula (VIIA):

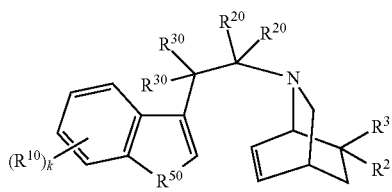
(VIIA)

wherein $C(R^{20})_2$ is $C=O$ is prepared comprising contacting a compound of Formula (VIIIA)

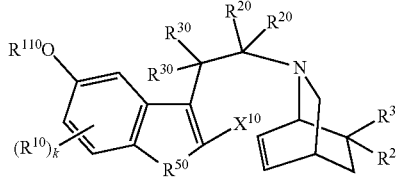
(VIIIA)

wherein $L^1$ is OH or another leaving group selected from halo, preferably chloro or bromo with a compound of Formula (IX):

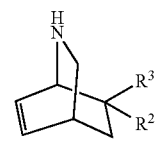
(IX)

under amide formation conditions to prepare the compound of Formula (VIIIA); or wherein the compound of Formula (VIIB):

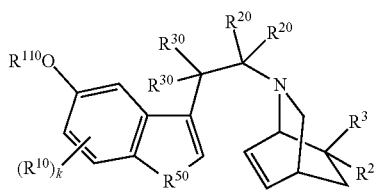
(VIIB)

wherein $C(R^{20})_2$ is $C=O$ is prepared comprising contacting a compound of Formula (VIIIB)

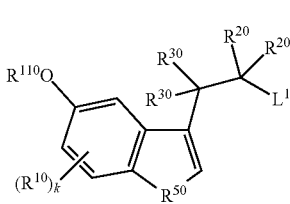
(VIIIB)

wherein L¹ is OH or another leaving group selected from halo, preferably chloro or bromo with a compound of Formula (IX):

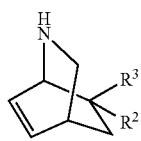

under amide formation conditions to prepare the compound of Formula (VIIB).

In one aspect, provided herein is a process of preparing a compound of formula (IV):

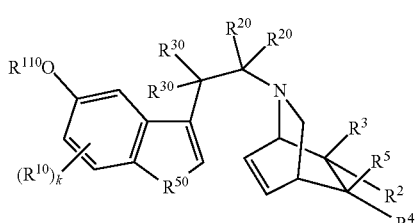

wherein $C(R^{20})_2$ is $CH_2$ is prepared comprising contacting a compound of Formula (VIIIC):

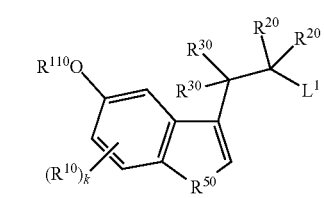

wherein L¹ is a leaving group with a compound of Formula (IX):

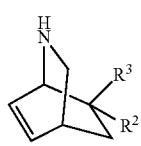

under nucleophilic substitution conditions to prepare the compound of Formula (IV); or wherein the compound of Formula (VIIC):

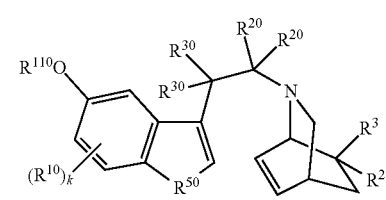

wherein $C(R^{20})_2$ is $CH_2$ is prepared comprising contacting a compound of Formula (VIIID)

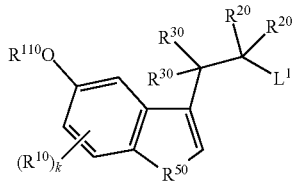

wherein L¹ is a leaving group with a compound of Formula (IX):

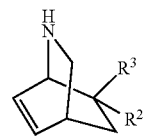

under nucleophilic substitution conditions to prepare the compound of Formula (VIIC).

Halogenation

In one aspect, provided herein is a process of preparing a compound of formula (IV):

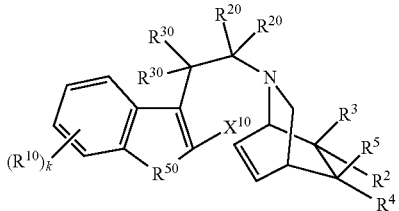

wherein $X^{10}$ is halo is prepared comprising contacting a compound of Formula (VIIA):

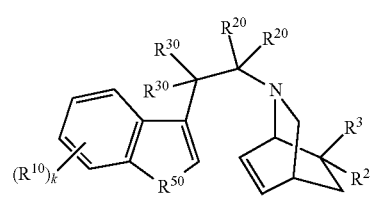

with a halogenating agent under conditions suitable for halogenation to provide the compound of Formula (IVA), or wherein the compound of Formula (VA)

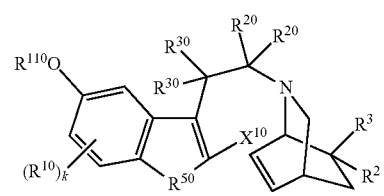

wherein $X^{10}$ is halo is prepared comprising contacting a compound of Formula (VIIB):

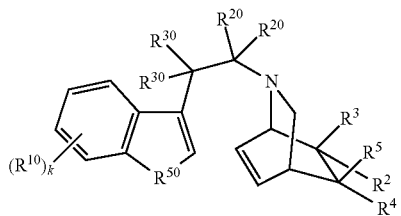

(VIIB)

with a halogenating agent under conditions suitable for halogenation to provide the compound of formula (VA).

As will be apparent to the skilled artisan, amides prepared as above can be reduced to the corresponding -$CH_2$-N< compounds by reacting with borohydrides or aluminum hydrides under reducing conditions.

Hydrogenation

In one aspect, provided herein is a method of subjecting a compound of formula:

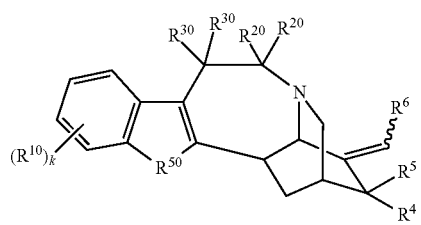

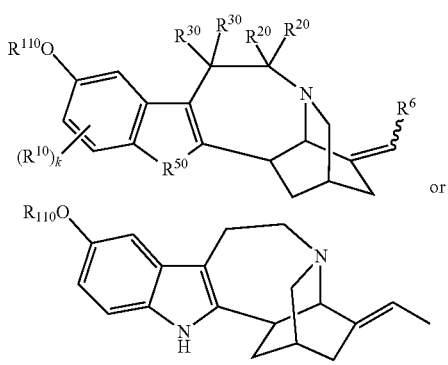

under hydrogenation condition to provide a compound of formula:

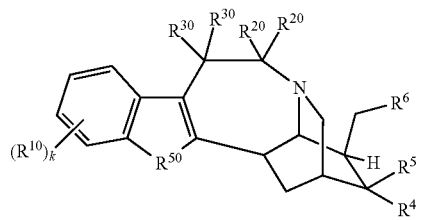

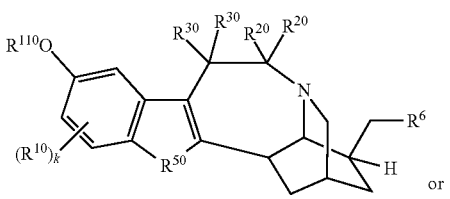

or

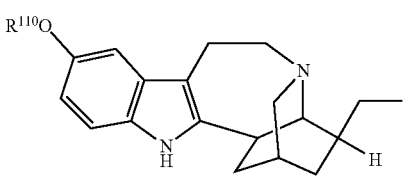

respectively.

Nenitzescu Reaction

In another aspect, provided here is a method of making a compound of formula:

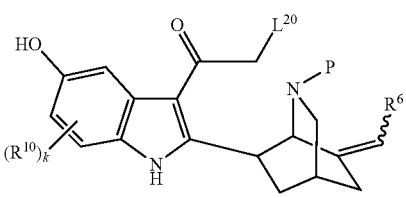

such as:

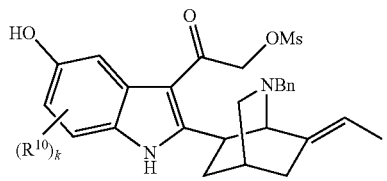

wherein $R^{10}$ is defined as in any embodiment herein, k is 0, 1, or 2, $L^{20}$ is a leaving group, preferably tosyl, mesyl, or another sulfonate, and P is a nitrogen protecting group, preferably, benzyl, comprising contacting a compound of formula:

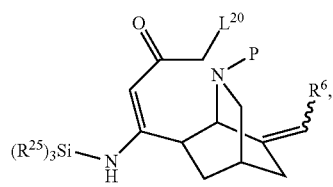

such as

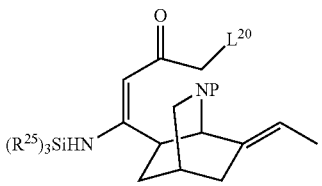

where each $R^{25}$ independently is $C_1$-$C_6$ alkyl or $C_6$-$C_{10}$ aryl, preferably phenyl, with a compound of formula:

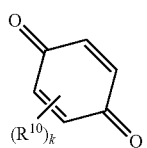

under Nenitzescu indole formation condition to provide a compound of formula:

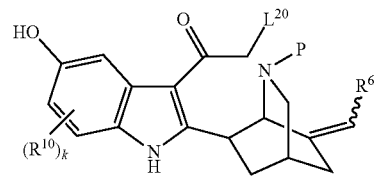

In one embodiment, the compound provided is of formula:

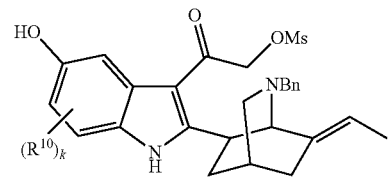

The protected alpha, beta unsaturated keto amine is reacted at a slight to about 2 fold molar excess of the quinone. Lewis acid catalysts may be employed optionally.

Other non limiting methods and intermediated are shown below:

Illustrative Nenitzescu and Fischer Indole Syntheses

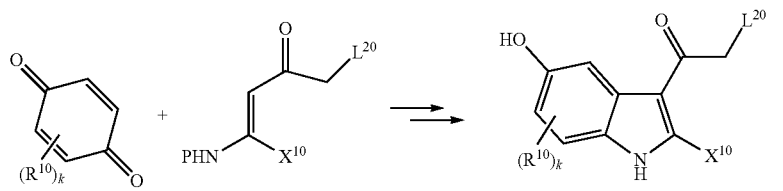

$L^{20}$ = alkoxy, halogen, OTs and the likes
$X^{10}$ = Cl, Br, I

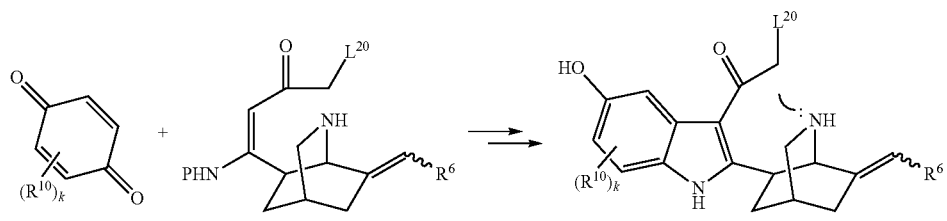

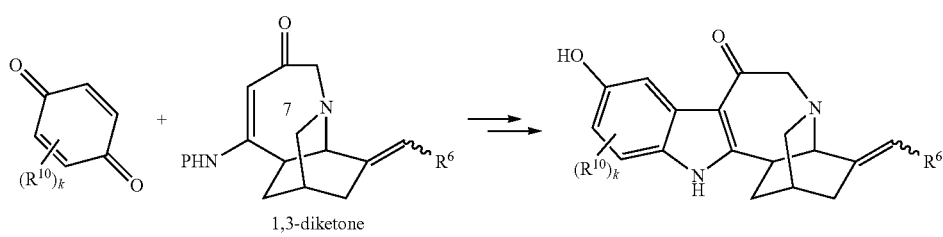

1,3-diketone

1) $NaBH_4$
2) p-TsOH

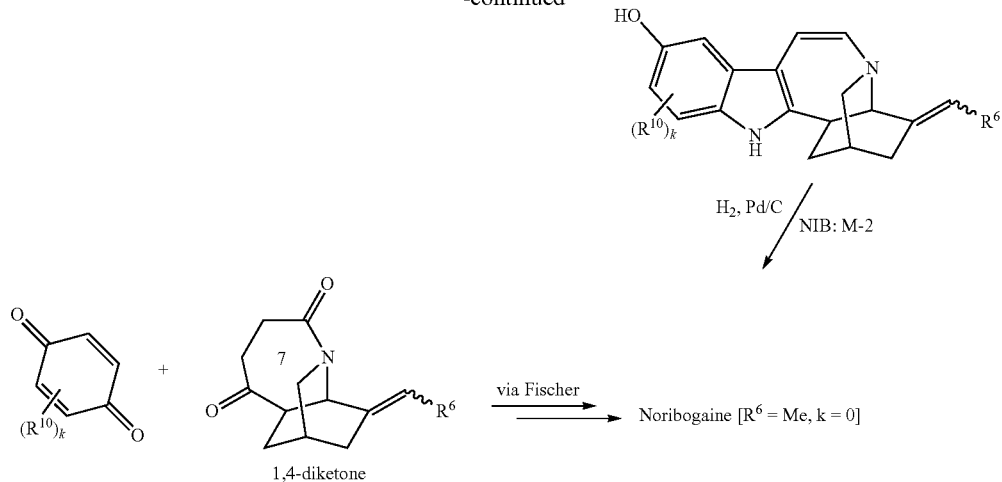

In one embodiment, $C(R^{20})_2$ is $CH_2$. In another embodiment, $C(R^{20})_2$ is $C=O$. A compound hereinabove, wherein $C(R^{20})_2$ is $C=O$ can be converted to one wherein $C(R^{20})_2$ is $CH_2$ upon contacting with a reducing agent under reduction conditions.

In one embodiment, $R^{110}$ is benzyl or a substituted benzyl group that is deprotected to provide a compound with $R^{110}$ being hydrogen upon hydrogenation.

In one embodiment, X10 is halo.

In one embodiment, $R^4$, $R^5$, $R^{20}$, and $R^{30}$ are hydrogen.

In another embodiment, $R^{50}$ is $NR^{51}$. In one embodiment, $R^{50}$ is NH. In another embodiment, $R^{50}$ is O.

In another embodiment, $CR^2R^3$ is $=$CHMe.

In another embodiment, k is 0. In another embodiment, k is 0 and preferably, the phenyl ring is substituted with the $-O-R^{110}$ group. In another embodiment, $R^{110}$ is $C_1$-$C_6$ alkyl optionally substituted with 1-3 substituents selected from phenyl optionally substituted with 1-3 substituents selected from the group consisting of $C_1$-$C_6$ alkyl and $C_1$-$C_6$ alkoxy.

Starting materials useful for preparing the compounds and in the processes provided herein are well known in the art and available commercially, for example, from Sigma-Aldrich Co. The reactions are carried out under suitable conditions to effect reaction completion. Typically, the reaction is carried out in an inert solvent for a period of time sufficient to provide a substantial amount of the product, which can be ascertained by using routine methods such as thin layer chromatography, $^1$H-nuclear magnetic resonance (NMR) spectroscopy, and the likes. As the skilled artisan will know or can ascertain based on this disclosure, certain reactions can be heated. As the skilled artisan will also understand, certain functionalities may have to be protected with protecting groups during one or more preparative steps and eventually deprotected. The product can be isolated and optionally purified using standard purification techniques, such as liquid chromatography, crystallization, and precipitation, or the products may be used for a subsequent reaction without further purification. Procedures useful in this invention is disclosed in PCT patent application publication nos. WO 2013/112757 and WO 2013/112622, which can be adapted in view of this disclosure to prepare compounds and in methods provided herein.

EXAMPLES

Certain illustrative and non-limiting processes of synthesizing certain compounds provided herein are schematically disclosed below.

Example 1

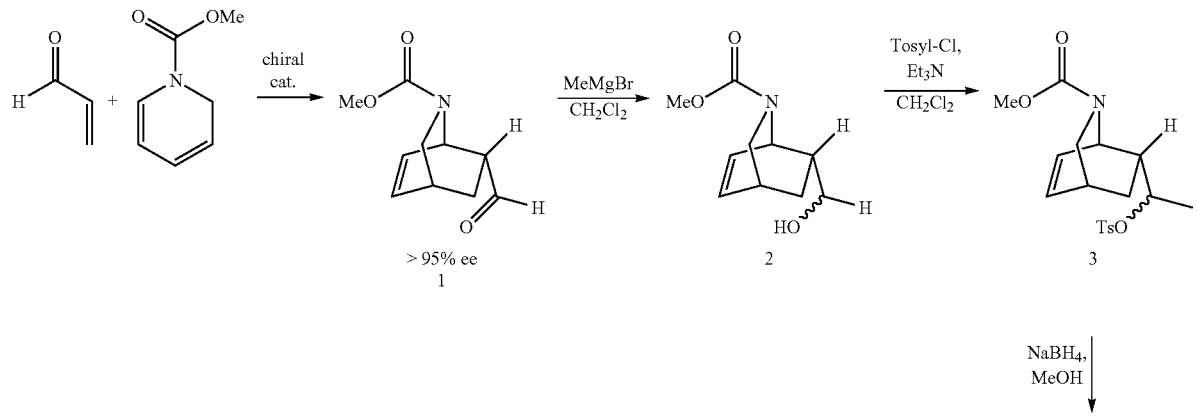

-continued
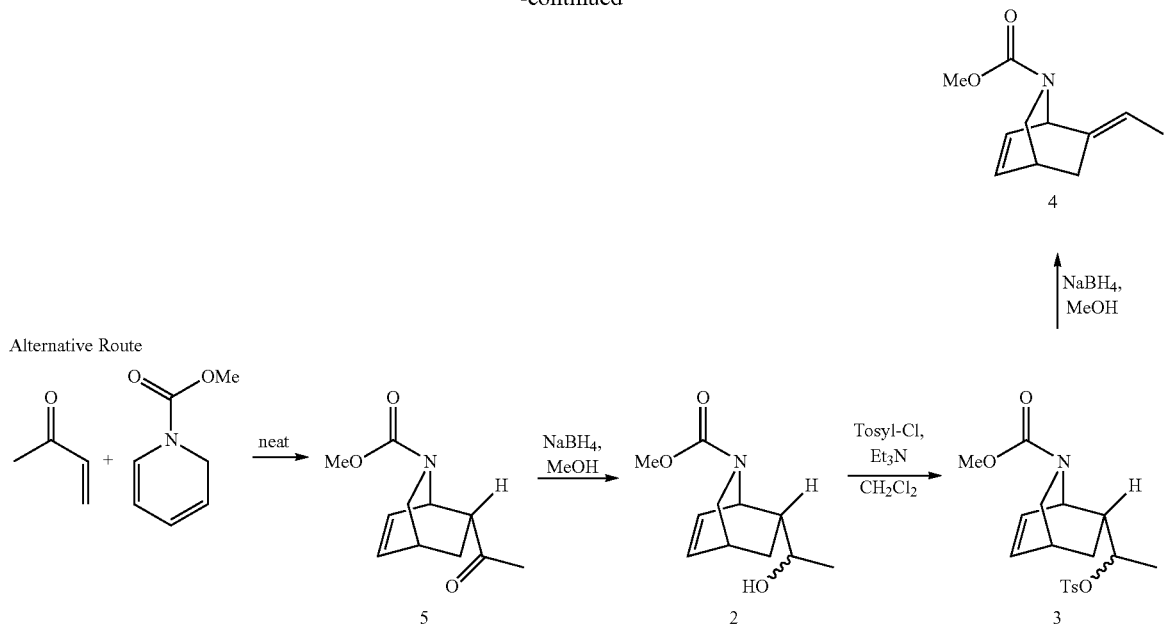
In addition to the selective approach, compound 4 can be made as a racemic mixture (by the alternative route). It is contemplated that the enantiomers of compound 4 can be separated via diastereomeric salt formation through the nitrogen atom or chiral high-performance column chromatography (HPLC), as would be well known to the skilled artisan.
Example 2
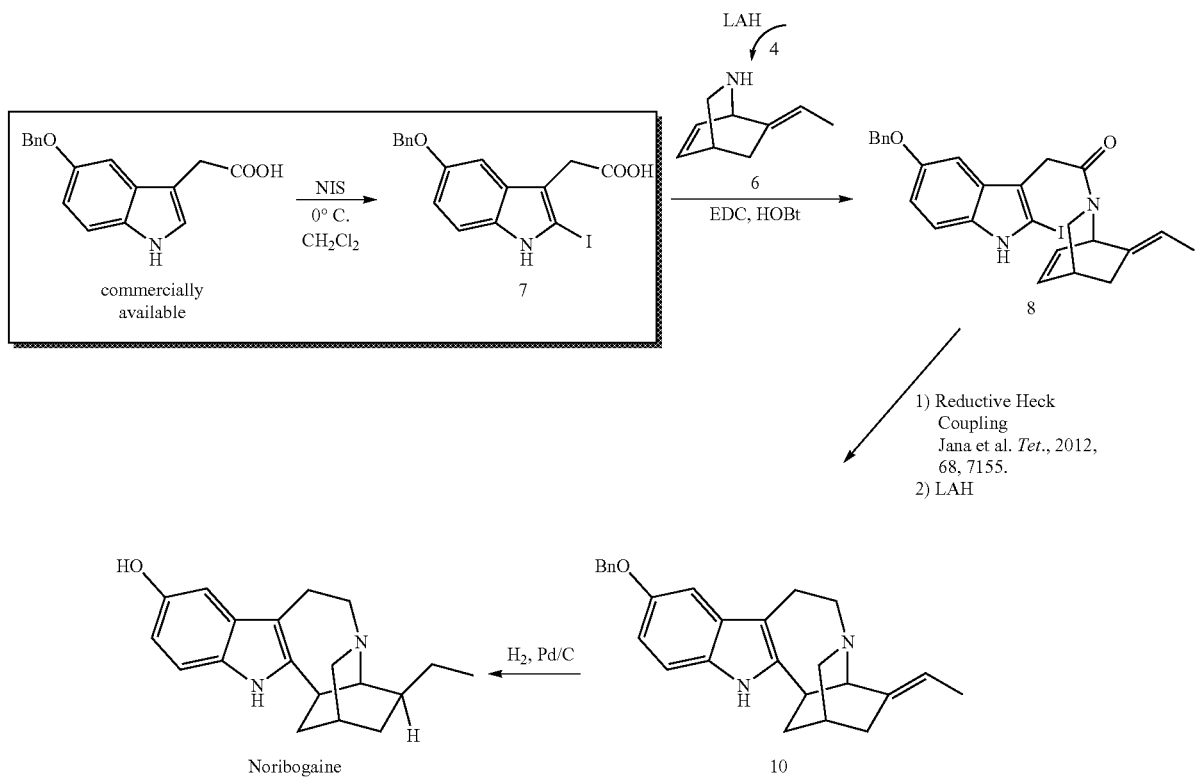

Example 3

Nucleophilic Substitution

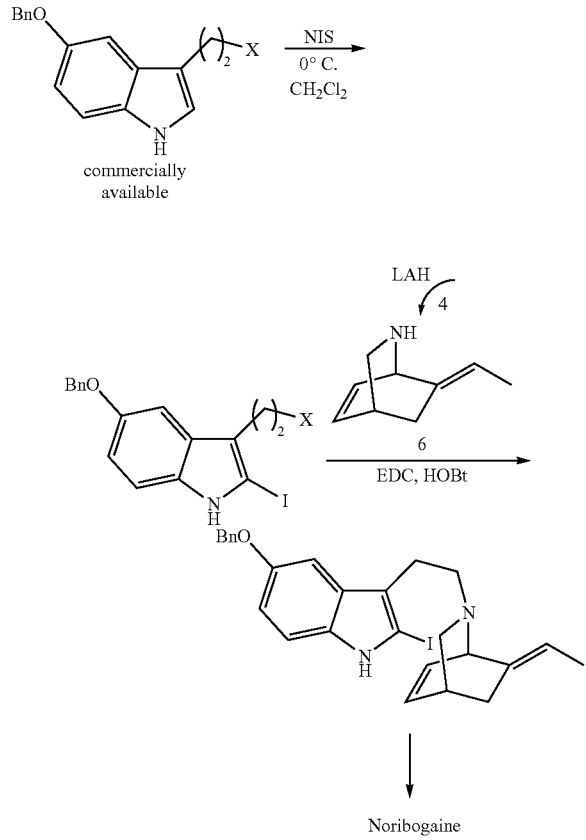

X = I, Br, Cl, O-Protecting group, O-Leaving group

Example 4

Nenitzescu Variation

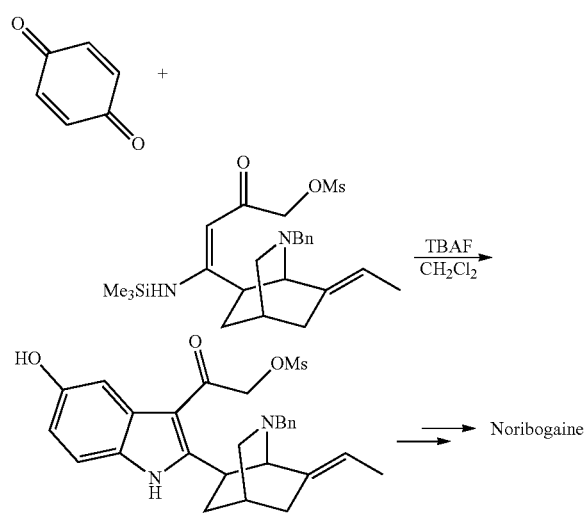

The invention claimed is:

1. A compound of Formula (I):

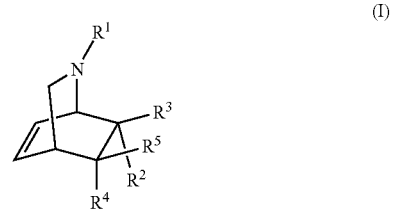

or a tautomer thereof or a salt of each thereof wherein
$R^1$ is selected from the group consisting of hydrogen, —$CO_2R^{11}$, —$COR^{12}$, —$C(R^{13})_3$, an amine protecting group, and

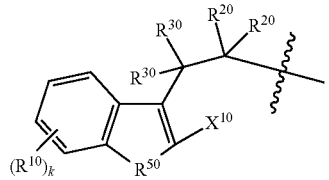

$R^{11}$ is selected from the group consisting of $C_1$-$C_6$ alkyl optionally substituted with 1-3 substituents selected from $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof, $C_2$-$C_6$ alkenyl, $C_2$-$C_6$ alkynyl, $C_6$-$C_{10}$ aryl, $C_2$-$C_{10}$ heteroaryl, $C_3$-$C_8$ cycloalkyl, and $C_3$-$C_8$ heterocyclyl, $R^{12}$ and $R^{13}$ independently are selected from the group consisting of hydrogen, $C_1$-$C_6$ alkyl optionally substituted with 1-3 substituents selected from $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof, $C_2$-$C_6$ alkenyl, $C_2$-$C_6$ alkynyl, $C_6$-$C_{10}$ aryl, $C_2$-$C_{10}$ heteroaryl, $C_3$-$C_8$ cycloalkyl, and $C_3$-$C_8$ heterocyclyl;

k is 0, 1, 2, or 3;

each $R^{10}$ is independently a substituent selected from the group consisting of —$OCOR^{11}$; and —$OCO_2R^{11}$, halo, amino, hydroxy, $C_1$-$C_6$ alkoxy, $C_1$-$C_6$ alkyl, $C_2$-$C_6$ alkenyl, $C_2$-$C_6$ alkynyl, cyano, nitro, —$N_3$, and —$CO_2H$ or an ester thereof, wherein the alkyl, alkoxy, alkenyl, or the alkylnyl group is optionally substituted with 1-3 substituents selected from the group consisting of keto, halo, amino, hydroxy, cyano, nitro, —$N_3$, phenyl optionally substituted with 1-3 substituents selected from the group consisting of $C_1$-$C_6$ alkyl and $C_1$-$C_6$ alkoxy, and —$CO_2H$ or an ester thereof;

$R^{20}$ is hydrogen or $C(R^{20})_2$ is a keto group;

$R^{30}$ is selected from the group consisting of hydrogen, halo, $C_1$-$C_6$ alkyl, $C_2$-$C_6$ alkenyl, $C_2$-$C_6$ alkynyl, wherein the alkyl, alkenyl, or the alkylnyl group is optionally substituted with 1-3 substituents selected from the group consisting of keto, halo, amino, hydroxy, cyano, nitro, —$N_3$, and —$CO_2H$ or an ester thereof;

$R^{50}$ is selected from the group consisting of —O— and N—$R^{51}$; and $R^{51}$ is selected from the group consisting of hydrogen and $C_1$-$C_6$ alkyl optionally substituted with 1-3 substituents selected from the group consisting of keto, halo, amino, hydroxy, cyano, nitro, —$N_3$, and —$CO_2H$ or an ester thereof;

$X^{10}$ is a leaving group, or is —OH or hydrogen;

$R^4$ and $R^5$ independently are selected from the group consisting of hydrogen, halo, $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, vinyl, ethynyl, and $CO_2H$ or an ester thereof;

$R^2$ and $R^3$ together with the carbon atom they are bonded to, form a =$CHR^6$ moiety;

$R^6$ is $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, or $C_3$-$C_8$ heterocyclyl;

wherein the cycloalkyl, heterocyclyl, aryl, or heteroaryl, is optionally substituted with 1-3 substituents selected from the group consisting of $C_1$-$C_6$ alkyl, $C_2$-$C_6$ alkenyl, $C_2$-$C_6$ alkynyl, $C_6$-$C_{10}$ aryl, cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof.

2. The compound of claim 1, of Formula (III):

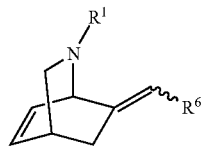

(III)

wherein ⌇ refers to a cis or a trans stereochemistry and $R^1$ is defined as in claim 1.

3. The compound of claim 2, wherein $R^1$ is hydrogen or $CO_2R^{11}$ and $R^{11}$ is $C_1$-$C_6$ alkyl.

4. The compound of claim 1 of Formula (IV):

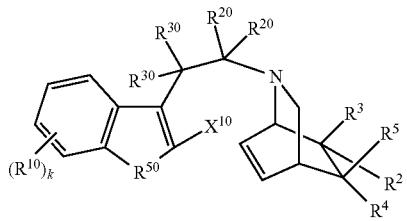

(IV)

wherein the variables are defined as in claim 1.

5. The compound of claim 1 of Formula (IVA):

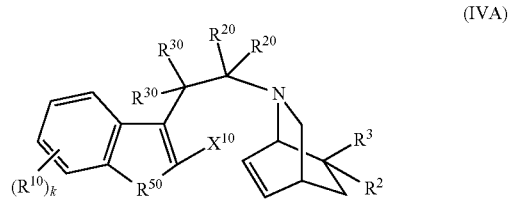

(IVA)

wherein the variables are defined as in claim 1 above.

6. The compound of claim 1 of Formula (IVB):

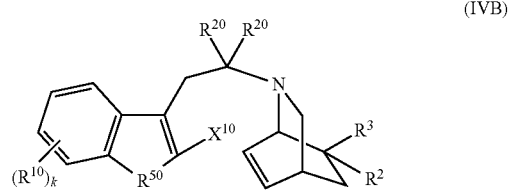

(IVB)

wherein the variables are defined as in claim 1 above.

7. The compound of claim 1 of Formula (IVC):

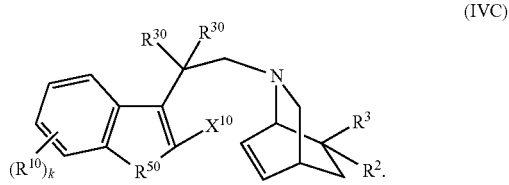

(IVC)

8. The compound of claim 1 of Formula (VA):

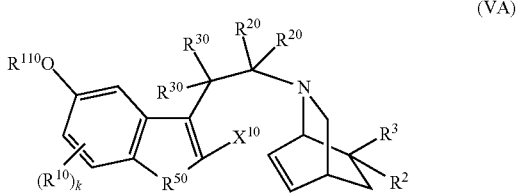

(VA)

wherein $R^{110}$ is selected from the group consisting of hydrogen;

$C_1$-$C_6$ alkyl optionally substituted with 1-3 substituents selected from the group consisting of halo, amino, hydroxy, cyano, nitro, —$N_3$, —$CO_2H$ or an ester thereof, and phenyl optionally substituted with 1-3 substituents selected from the group consisting of $C_1$-$C_6$ alkyl and $C_1$-$C_6$ alkoxy;

—$COR^{11}$; and

—$CO_2R^{11}$;

k is 0, 1 or 2;

and the remaining variables are defined as in claim 1 above.

9. A compound of Formula (VB):

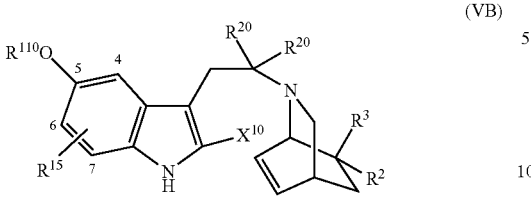

(VB)

wherein $X^{10}$ is a leaving group, or is —OH or hydrogen, and the remaining variables are as tabulated below:

| $R^{15}$ | $R^{110}$ | $C(R^{20})_2$ | $CR^2R^3$ |
|---|---|---|---|
| H, 4-Me, 6-Me, 7-Me, 4-OH, 6-OH, 7-OH, 4-OMe, 6-OMe, or 7-OMe | Bn | C=O | $CR^2R^3$ is $C=CR^{48}H$, where $R^{48}$ is Me, Et, Pr, or Bu |
| H, 4-Me, 6-Me, 7-Me, 4-OH, 6-OH, 7-OH, 4-OMe, 6-OMe, or 7-OMe | Bn | $CH_2$ | $CR^2R^3$ is $C=CR^{48}H$, where $R^{48}$ is Me, Et, Pr, or Bu | or

| $R^{15}$ | $R^{110}$ | $C(R^{20})_2$ | $R^2$ | $R^3$ | $R^{47}$ |
|---|---|---|---|---|---|
| H, 4-Me, 6-Me, 7-Me, 4-OH, 6-OH, 7-OH, 4-OMe, 6-OMe, or 7-OMe | Bn | C=O | $CH_2CH_2R^{47}$ | H | $C_1$-$C_4$ alkyl optionally substituted with an OMe group, OH group, an amide or with an amino group |
| H, 4-Me, 6-Me, 7-Me, 4-OH, 6-OH, 7-OH, 4-OMe, 6-OMe, or 7-OMe | Bn | $CH_2$ | $CH_2CH_2R^{47}$ | H | $C_1$-$C_4$ alkyl optionally substituted with an OMe group, OH group, an amide or with an amino group |
| H, 4-Me, 6-Me, 7-Me, 4-OH, 6-OH, 7-OH, 4-OMe, 6-OMe, or 7-OMe | H | C=O | $CH_2CH_2R^{47}$ | H | $C_1$-$C_4$ alkyl optionally substituted with an OMe group, OH group, an amide or with an amino group |
| H, 4-Me, 6-Me, 7-Me, 4-OH, 6-OH, 7-OH, 4-OMe, 6-OMe, or 7-OMe | H | $CH_2$ | $CH_2CH_2R^{47}$ | H | $C_1$-$C_4$ alkyl optionally substituted with an OMe group, OH group, an amide or with an amino group. |

10. The compound of claim 1 of formula;

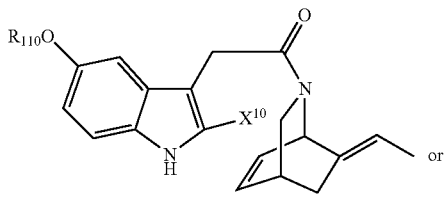

or

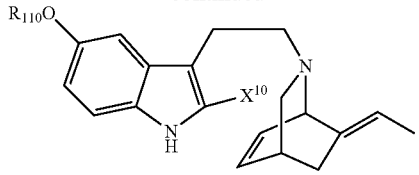

wherein $X^{10}$ is hydrogen, chloro, bromo, or iodo, and wherein $R^{110}$ is selected from the group consisting of hydrogen;
$C_1$-$C_6$ alkyl optionally substituted with 1-3 substituents selected from the group consisting of halo, amino, hydroxy, cyano, nitro, —$N_3$, —$CO_2H$ or an ester thereof, and phenyl optionally substituted with 1-3 substituents selected from the group consisting of $C_1$-$C_6$ alkyl and $C_1$-$C_6$ alkoxy;
—$COR^{11}$; and
—$CO_2R^{11}$,
and wherein the remaining variables are as defined in claim 1.

11. The compound of claim 1, wherein the leaving group is halo or —$OSO_2R^{71}$, wherein
$R^{71}$ is $C_1$-$C_6$ alkyl optionally substituted with 1-3 substituents selected from the group consisting of $C_6$-$C_{10}$ aryl, $C_3$-$C_8$ cycloalkyl, $C_2$-$C_{10}$ heteroaryl, or is $C_3$-$C_8$ heterocyclyl, $C_6$-$C_{10}$ aryl, $C_3$-$C_8$ cycloalkyl, $C_2$-$C_{10}$ heteroaryl, or $C_3$-$C_8$ heterocyclyl;
wherein the cycloalkyl, heterocyclyl, aryl, or heteroaryl, is optionally substituted with 1-3 substituents selected from the group consisting of $C_1$-$C_6$ alkyl, $C_2$-$C_6$ alkenyl, $C_2$-$C_6$ alkynyl, $C_6$-$C_{10}$ aryl, cycloalkyl, $C_2$-$C_{10}$ heteroaryl, $C_3$-$C_8$ heterocyclyl, halo, amino, —$N_3$, hydroxy, $C_1$-$C_6$ alkoxy, silyl, nitro, cyano, and $CO_2H$ or an ester thereof.

12. The compound of claim 1, wherein the leaving group is bromo or iodo.

13. The compound of claim 9, wherein $R^{47}$ is selected from Me, Et, Pr, Bu, $CH_2OMe$, $(CH_2)_2OMe$, $(CH_2)_3OMe$, $(CH_2)_4OMe$, $CH_2OH$, $(CH_2)_2OH$, $(CH_2)_3OH$, $(CH_2)_4OH$, $(CH_2)_2NHCOMe$, $(CH_2)_3NHCOMe$, $(CH_2)_4NHCOMe$, $CO_2(CH_2)_2NMe_2$,

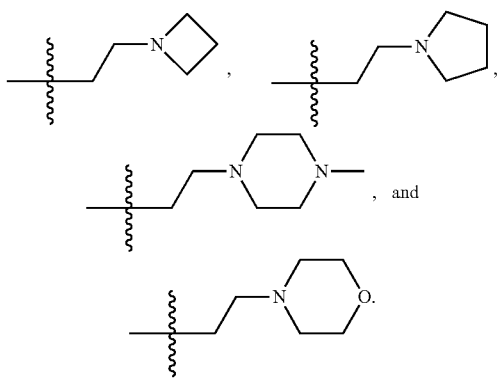

* * * * *